US012053546B2

(12) United States Patent
Toledano et al.

(10) Patent No.: US 12,053,546 B2
(45) Date of Patent: Aug. 6, 2024

(54) STABILIZED TOPICAL FORMULATIONS CONTAINING CORE-SHELL MICROCAPSULES

(75) Inventors: Ofer Toledano, Kfar Saba (IL); Haim Bar-Simantov, Netanya (IL); Hanan Sertchook, Gedera (IL)

(73) Assignee: Sol-Gel Technologies Ltd., Ness Ziona (IL)

( * ) Notice: Subject to any disclaimer, the term of this patent is extended or adjusted under 35 U.S.C. 154(b) by 0 days.

(21) Appl. No.: 13/537,646

(22) Filed: Jun. 29, 2012

(65) Prior Publication Data

US 2013/0095185 A1 Apr. 18, 2013

Related U.S. Application Data

(60) Provisional application No. 61/502,725, filed on Jun. 29, 2011.

(51) Int. Cl.
| | | |
|---|---|---|
| A61K 9/107 | (2006.01) | |
| A61K 9/00 | (2006.01) | |
| A61K 9/06 | (2006.01) | |
| A61K 9/50 | (2006.01) | |
| A61K 31/203 | (2006.01) | |
| A61K 31/327 | (2006.01) | |
| A61K 47/14 | (2017.01) | |

(52) U.S. Cl.
CPC ............ *A61K 9/107* (2013.01); *A61K 9/0014* (2013.01); *A61K 9/06* (2013.01); *A61K 9/501* (2013.01); *A61K 9/5084* (2013.01); *A61K 31/203* (2013.01); *A61K 31/327* (2013.01); *A61K 47/14* (2013.01)

(58) Field of Classification Search
None
See application file for complete search history.

(56) References Cited

U.S. PATENT DOCUMENTS

| | | | | |
|---|---|---|---|---|
| 5,401,517 | A | * | 3/1995 | Meyers et al. ................ 424/401 |
| 5,468,471 | A | * | 11/1995 | Zecchino et al. .............. 424/59 |
| 5,500,223 | A | | 3/1996 | Behan et al. |
| 5,690,923 | A | | 11/1997 | DeVringer et al. |
| 5,720,949 | A | * | 2/1998 | Davis ........................ 424/78.03 |
| 5,891,476 | A | | 4/1999 | Reo et al. |
| 6,238,650 | B1 | | 5/2001 | Lapidot et al. |
| 6,270,836 | B1 | | 8/2001 | Holman |
| 6,303,149 | B1 | | 10/2001 | Magdassi et al. |
| 6,337,089 | B1 | | 1/2002 | Yoshioka et al. |
| 6,436,375 | B1 | | 8/2002 | Lapidot et al. |
| 6,468,509 | B2 | | 10/2002 | Lapidot et al. |
| 6,939,552 | B2 | | 9/2005 | Ansara et al. |
| 6,979,440 | B2 | * | 12/2005 | Shefer .................. A61K 8/0204 424/78.02 |
| 8,158,109 | B2 | | 4/2012 | Abram et al. |
| 8,617,580 | B2 | | 12/2013 | Toledano et al. |
| 9,868,103 | B2 | | 1/2018 | Toledano et al. |
| 10,512,796 | B2 | | 12/2019 | Toledano et al. |
| 2002/0064541 | A1 | | 5/2002 | Lapidot et al. |
| 2003/0082217 | A1 | | 5/2003 | Afriat et al. |
| 2003/0157330 | A1 | | 8/2003 | Ostafin et al. |
| 2004/0096419 | A1 | * | 5/2004 | Golz-Berner ............ A61K 8/11 424/74 |
| 2004/0202726 | A1 | * | 10/2004 | DeShay .............. A61K 36/8962 424/679 |
| 2006/0014834 | A1 | | 1/2006 | Vishnupad et al. |
| 2007/0207113 | A1 | | 9/2007 | Joerger et al. |
| 2009/0130220 | A1 | * | 5/2009 | Johnson ................. A61K 8/922 424/539 |
| 2009/0226380 | A1 | | 9/2009 | Clark et al. |
| 2010/0016443 | A1 | | 1/2010 | Toledano et al. |
| 2010/0029765 | A1 | | 2/2010 | Gupta et al. |
| 2010/0047357 | A1 | * | 2/2010 | Toledano et al. ............. 424/490 |
| 2010/0203121 | A1 | | 8/2010 | Toledano et al. |
| 2010/0255107 | A1 | | 10/2010 | Lapidot et al. |
| 2011/0177951 | A1 | | 7/2011 | Toledano et al. |
| 2013/0095185 | A1 | | 4/2013 | Toledano et al. |
| 2018/0101284 | A1 | | 4/2018 | Pope et al. |
| 2018/0117369 | A1 | | 5/2018 | Toledano et al. |
| 2018/0207451 | A1 | | 7/2018 | Toledano et al. |
| 2018/0339176 | A1 | | 11/2018 | Toledano et al. |
| 2020/0114327 | A1 | | 4/2020 | Toledano et al. |

(Continued)

FOREIGN PATENT DOCUMENTS

| | | |
|---|---|---|
| DE | 102004017221 A1 | 10/2005 |
| GB | 1450507 A | 9/1976 |
| JP | 2003534249 A | 11/2003 |

(Continued)

OTHER PUBLICATIONS

Dr. Darrin Lew "physical properties of beeswax and paraffin wax" (https://www.drdarrinlew.us/global-warming/physical-properties-of-beeswax-and-paraffin-wax.html) no pagination, 2023.*
American heritage dictionary, "room temperature" (https://www.ahdictionary.com/word/search.html?q=room+temperature), no pagination, accessed Mar. 23, 2024.*
Extended European Search Report dated Nov. 21, 2014, in corresponding European Application No. EP 12 80 4460.
Bon et al., "Pickering Stabilization as a Tool in the Fabrication of Complex Nanopatterned Silica Microcapsules", Langmuir, 23: 9527-9530, (Aug. 2007).
Prestidge et al. "Nanoparticle encapsulation of emulsion droplets", International Journal of Pharmaceutics 324:92-100, (Jul. 2006).
Jenning et al "Comparison of wax and glyceride solid lipid nanoparticles (SLN)" International Journal of Pharmaceutics, 196: 219-222 (2000).

(Continued)

*Primary Examiner* — Erin E Hirt
(74) *Attorney, Agent, or Firm* — Mark S. Cohen; PEARL COHEN ZEDEK LATZER BARATZ LLP

(57) ABSTRACT

The present disclosure relates to compositions for topical application, where the compositions comprise microcapsules having a core that comprises benzoyl peroxide and a shell that comprises an inorganic polymer, microcapsules having a core that comprises a retinoid and a shell that comprises an inorganic polymer, and a stabilizing agent. The composition can be in a variety of forms, such as emulsion and gel.

18 Claims, 5 Drawing Sheets

(56) References Cited

U.S. PATENT DOCUMENTS

2020/0383927 A1 12/2020 Toledano et al.
2021/0007996 A1 1/2021 Toledano et al.

FOREIGN PATENT DOCUMENTS

| WO | 0180823 A2 | 11/2001 | |
|---|---|---|---|
| WO | 03034979 A2 | 5/2003 | |
| WO | WO-03034979 A2 * | 5/2003 | ............ A61K 8/042 |
| WO | 2004081222 A2 | 9/2004 | |
| WO | WO-2005009604 A1 | 2/2005 | |
| WO | 2005097056 A1 | 10/2005 | |
| WO | 2007015243 A2 | 2/2007 | |
| WO | WO-2007015243 A2 | 2/2007 | |
| WO | 2008072239 A2 | 6/2008 | |
| WO | 2008093346 A2 | 8/2008 | |
| WO | WO-2008093347 A2 | 8/2008 | |
| WO | 2008133482 A1 | 11/2008 | |
| WO | 2008134908 A1 | 11/2008 | |
| WO | WO-2009051839 A1 | 4/2009 | |
| WO | 2010013250 A2 | 2/2010 | |
| WO | WO-2010013250 A2 * | 2/2010 | ............ A01N 25/28 |
| WO | 2011080741 A2 | 7/2011 | |
| WO | WO-2011080741 A2 | 7/2011 | |

OTHER PUBLICATIONS

Jenning et al. "Encapsulation of retinoids in solid lipid nanoparticles (LN)" J. Microencapsulation, 18:149-152 (2001).
"Viscosity" 1-20; www.saylor.org/site/wp-content/uploads/2011/04/Viscosity.pdf (Apr. 2011).
"Viscosity Chart" Flux—http://thesuccesstechnic.weebly.com/uploads/7/2/1/3/7213446/flux-high-viscosity-b0000-visc-chart-1.pdf downloaded Jun. 16, 2015.
Buerkle Gmbh "Viscosity of Liquids" https://www.buerkle.de/media/files/Downloads/Viscosity_EN.pdf 2011.
"Viscosity Scales" Smooth-On files.smooth-on.com/viscosity_chart.pdf; downloaded Jun. 16, 2015.
U.S. Pharmacopeia USP29 "Pastes" downloaded on Sep. 25, 2015 from http://www.pharmacopeia.cn.
Rowe et al. eds, Handbook of Pharmaceutical Excipients, Sixth edition, Pharmaceutical Press (2009).
Büchel, G., Grün, M., Unger, K. K., Matsumoto, A., & Kazuo, T. (1998). Tailored syntheses of nanostructured silicas: control of particle morphology, particle size and pore size. Supramolecular Science, 5(3-4), 253-259.
Date, A. A., Naik, B., & Nagarsenker, M. S. (2006). Novel drug delivery systems: potential in improving topical delivery of antiacne agents. Skin Pharmacology and Physiology, 19(1), 2-16.
Fat and why it matters—"The kinds of fats and why it matters to you", Indiana University, Copyright 2019, http://www.indiana.edu/~oso/Fat/Definitions.html.
He, J., Fujikawa, S., Kunitake, T., & Nakao, A. (2003). Preparation of porous and nonporous silica nanofilms from aqueous sodium silicate. Chemistry of materials, 15(17), 3308-3313.
Huo, Q., Feng, J., Schüth, F., & Stucky, G. D. (1997). Preparation of hard mesoporous silica spheres. Chemistry of Materials, 9(1), 14-17.
Nooney, R. I., Thirunavukkarasu, D., Chen, Y., Josephs, R., & Ostafin, A. E. (2002). Synthesis of nanoscale mesoporous silica spheres with controlled particle size. Chemistry of materials, 14(11), 4721-4728.
Nooney, R. I., Thirunavukkarasu, D., Chen, Y., Josephs, R., & Ostafin, A. E. (2003). Self-assembly of mesoporous nanoscale silica/gold composites. Langmuir, 19(18), 7628-7637.
Ozin, G. A. (1992). Nanochemistry: synthesis in diminishing dimensions. Advanced Materials, 4(10), 612-649.
Škapin, S. D., & Matijević, E. (2004). Preparation and coating of finely dispersed drugs: 4. Loratadine and danazol. Journal of colloid and interface science, 272(1), 90-98.
Tjandra, W., Yao, J., & Tam, K. C. (2006). Interaction between silicates and ionic surfactants in dilute solution. Langmuir, 22(4), 1493-1499.
Atralin™ (Tretinoin) (2007) Gel prescribing information, FDA, Coria Laboratories Ltd., Jul. 2007, 9 pages.
Del Rosso, J. Q Et al. (2010). Absence of degradation of tretinoin when benzoyl peroxide is combined with an optimized formulation of tretinoin gel (0.05%). *The Journal of Clinical and Aesthetic Dermatology*, 3(10), 26.
Binks, B. P. et al. (2005). Nanoparticle silica-stabilised oil-in-water emulsions: improving emulsion stability. *Colloids and Surfaces A: Physicochemical and Engineering Aspects*, 253(1-3), 105-115.
Patel, V. B. et al. (2001). Clinical assessment of the combination therapy with liposomal gels of tretinoin and benzoyl peroxide in acne. *AAPS PharmSciTech*, 2(3), 1-5.
Bartlett, P. D. et al. (1947). The decomposition of benzoyl peroxide in solvents. II. Ethers, alcohols, phenols and amines. Journal of the American chemical society, 69(10), 2299-2306.
Shen, S. L. et al. (2007). A novel process to synthesize magnetic hollow silica microspheres. Colloids and Surfaces A: Physicochemical and Engineering Aspects, 311(1-3), 99-105.

* cited by examiner

… … …

STABILIZED TOPICAL FORMULATIONS CONTAINING CORE-SHELL MICROCAPSULES

RELATED APPLICATION INFORMATION

This application claims the benefit of U.S. Provisional Application Ser. No. 61/502,725, filed Jun. 29, 2011, which is hereby incorporated by reference in its entirety.

BACKGROUND

1. Field of the Invention

The present invention relates to compositions for topical application, and particularly compositions of stabilized topical formulations containing core-shell microcapsules.

2. Description of the Related Art

Microcapsules having a core surrounded within a metal oxide shell have been proposed as controlled forms of topically administered compositions. It has been shown that various active agents, such as anti-acne agents, can be encapsulated within the metal oxide shell. For example, International Application No. PCT/IL/2008/000140 (published as WO 2008/093346) describes methods and compositions comprising benzoyl peroxide (BPO) and a retinoid, at least one of which and by some embodiments both are encapsulated by a silica-based shell. International Application No. PCT/IL2010/001092 (published as WO 2011/080741) describes methods and compositions utilizing microcapsules having a stabilized core with encapsulated active agents, such as benzoyl peroxide and/or all-trans retinoic acid (ATRA). Both these International Applications are hereby incorporated by reference in their entirety.

SUMMARY OF THE INVENTION

Various methods and compositions utilizing microcapsules having a stabilized core with encapsulated active agents are known. Although various embodiments of such compositions containing encapsulated BPO and encapsulated ATRA are useful for their intended purpose, during additional research and product development involving these and other microencapsulated BPO/retinoid compositions, it was discovered that some formulations exhibited certain shelf life problems, e.g., physical stability, retinoid stability and/or microbial content problems, particularly after long-term storage and/or elevated storage temperatures. The extent and source of these problems had not been previously recognized. For example, it was believed that compositions containing BPO would be unlikely to have microbial content problems because BPO is a strong oxidizing agent and effective antimicrobial. Initial attempts to address the microbial content problem by including an antimicrobial were complicated by the discovery that some antimicrobials resulted in retinoid degradation. Initial attempts to address the physical stability problem by including a surface active stabilizer in the composition were likewise complicated by the discovery that some stabilizers also resulted in retinoid degradation.

The inventors of the present invention have found that it is possible to provide compositions comprising both benzoyl peroxide and retinoid, each in separated encapsulated forms, having physical stability, retinoid stability and/or microbial stability.

In its first aspects the present invention provides a composition for topical application, comprising: a plurality of first core-shell microcapsules comprising a first core that comprises benzoyl peroxide and a first shell that comprises a first inorganic polymer; and a plurality of second core-shell microcapsules comprising a second core that comprises a retinoid and a second shell that comprises a second inorganic polymer; wherein said composition is an oil in water emulsion comprising a polyoxylstearate and a glycerylstearate wherein the ratio of said polyoxylstearate to said glycerylstearate is in the range of 0.1:10 to 10:0.1. In an embodiment, the ratio of said polyoxylstearate to said glycerylstearate is in the range of 1:10 to 10:1. In another embodiment, the ratio of said polyoxylstearate to said glycerylstearate is in the range of 1:5 to 5:1. In another embodiment, the ratio of said polyoxylstearate to said glycerylstearate is in the range of 2:3 to 3:2.

In a further aspect the invention provides a composition for topical application, comprising: a plurality of first core-shell microcapsules comprising a first core that comprises benzoyl peroxide and a first shell that comprises a first inorganic polymer; and a plurality of second core-shell microcapsules comprising a second core that comprises a retinoid and a second shell that comprises a second inorganic polymer; wherein said composition is in a gel form comprising at least one non-ionic polymeric dispersant and at least one thickening agent.

In yet a further aspect the invention provides a composition for topical application, comprising: a plurality of first core-shell microcapsules comprising a first core that comprises benzoyl peroxide and a first shell that comprises a first inorganic polymer; a plurality of second core-shell microcapsules comprising a second core that comprises a retinoid and a second shell that comprises a second inorganic polymer; and an amount of a stabilizing agent that is effective to: (i) maintain the amount of benzoyl peroxide and the amount of retinoid in the composition at a level that is at least about 90% of the initial amounts, as measured after storage of the composition at a storage condition of 30° C. for three months; and (ii) maintain the microbial count of the composition at a level that meets the criteria of USP 51, as measured by Antimicrobial Effectiveness Testing (AET) after storage of the composition at a storage condition of 40° C. for one month.

In yet a further aspect the invention provides a composition in a gel form for topical application, comprising: a plurality of first core-shell microcapsules comprising a first core that comprises benzoyl peroxide and a first shell that comprises a first silica polymer; a plurality of second core-shell microcapsules comprising a second core that comprises all-trans retinoic acid (ATRA) and a second shell that comprises a second silica polymer; and at least one non-ionic polymer in an amount effective to provide at least one stabilization selected from the group consisting of (i) viscosity stabilization whereby the viscosity of said composition is maintained such that the change in viscosity of said composition, as measured after manufacture followed by three months storage at 25° C., is less than about 30%, and (ii) degradation stabilization whereby the amount of degradation of said ATRA, as measured after manufacture followed by three months storage at 25° C., is less than about 10%.

In another aspect the invention provides a composition in an emulsion form for topical application, comprising: a plurality of first core-shell microcapsules comprising a first core that comprises benzoyl peroxide and a first shell that comprises a first silica polymer; a plurality of second core-shell microcapsules comprising a second core that comprises all-trans retinoic acid (ATRA) and a second shell that comprises a second silica polymer; and a stabilizing agent comprising at least one non-ionic surfactant and at least one antimicrobial in amounts effective to: (i) maintain the amount of benzoyl peroxide and the amount of retinoid in the composition at a level that is at least about 90% of the initial amounts, as measured after storage of the composition at a storage condition selected from the group consisting of 40° C. for two months, 30° C. for three months, 25° C. for six months and 5° C. for two years; and (ii) maintain the microbial count of the composition at a level that meets the criteria of USP 51, as measured by Antimicrobial Effectiveness Testing (AET) after storage of the composition at a storage condition of 40° C. for one month.

The invention also provides a composition in an emulsion form for topical application, comprising: a plurality of first core-shell microcapsules comprising a first core that comprises benzoyl peroxide and a first shell that comprises a first silica polymer, the benzoyl peroxide being present in the composition in an initial amount of about 6% by weight, based on the total weight of the composition; a plurality of second core-shell microcapsules comprising a second core that comprises all-trans retinoic acid (ATRA) and a second shell that comprises a second silica polymer, the ATRA being present in the composition in an initial amount of about 0.1% by weight, based on the total weight of the composition; and a stabilizing agent comprising (a) at least one non-ionic surfactant selected from the group consisting of polyoxyl 100 stearate and glycerol monostearate; and (b) at least one antimicrobial selected from the group consisting of methylparaben and imidazolidinyl urea; wherein the stabilizing agent is present in an amount effective to: (ia) maintain the amount of benzoyl peroxide at a level of at least about 5.4% by weight based on the total weight of the composition, as measured after storage of the composition at a storage condition selected from the group consisting of 40° C. for two months, 30° C. for three months, 25° C. for six months and 5° C. for two years; (ib) maintain the amount of ATRA at a level of at least about 0.09% by weight based on the total weight of the composition, as measured after storage of the composition at a storage condition selected from the group consisting of 40° C. for two months, 30° C. for three months, 25° C. for six months and 5° C. for two years; (ii) maintain the microbial count of the composition at a level that meets the criteria of USP 51, as measured by Antimicrobial Effectiveness Testing (AET) after storage of the composition at a storage condition of 40° C. for one month; and (iii) maintain the bulk viscosity of said composition at about one million cps or less and within a range of about 70% to about 130% of the initial bulk viscosity, as measured after storage of the composition at 25° C. for three months.

According to another one of its aspects the invention provides a composition in an emulsion form for topical application, comprising: a plurality of first core-shell microcapsules comprising a first core that comprises benzoyl peroxide and a first shell that comprises a first silica polymer, the benzoyl peroxide being present in the composition in an initial amount of about 3% by weight, based on the total weight of the composition; a plurality of second core-shell microcapsules comprising a second core that comprises all-trans retinoic acid (ATRA) and a second shell that comprises a second silica polymer, the ATRA being present in the composition in an initial amount of about 0.05% by weight, based on the total weight of the composition; and a stabilizing agent comprising (a) at least one non-ionic surfactant selected from the group consisting of polyoxyl 100 stearate and glycerol monostearate; and (b) at least one antimicrobial selected from the group consisting of methylparaben and imidazolidinyl urea; wherein the stabilizing agent is present in an amount effective to: (ia) maintain the amount of benzoyl peroxide at a level of at least about 2.7% by weight based on the total weight of the composition, as measured after storage of the composition at a storage condition selected from the group consisting of 40° C. for two months, 30° C. for three months, 25° C. for six months and 5° C. for two years; (ib) maintain the amount of ATRA at a level of at least about 0.045% by weight based on the total weight of the composition, as measured after storage of the composition at a storage condition selected from the group consisting of 40° C. for two months, 30° C. for three months, 25° C. for six months and 5° C. for two years; (ii) maintain the microbial count of the composition at a level that meets the criteria of USP 51, as measured by Antimicrobial Effectiveness Testing (AET) after storage of the composition at a storage condition of 40° C. for one month; and (iii) maintain the bulk viscosity of said composition at about one million cps or less and within a range of about 70% to about 130% of the initial bulk viscosity, as measured after storage of the composition at 25° C. for three months.

The invention further provides a packaged product, comprising a sealable container and a composition as described herein contained within the sealable container.

These aspects and other embodiments thereof are described in greater detail below.

DETAILED DESCRIPTION

Figure 1:
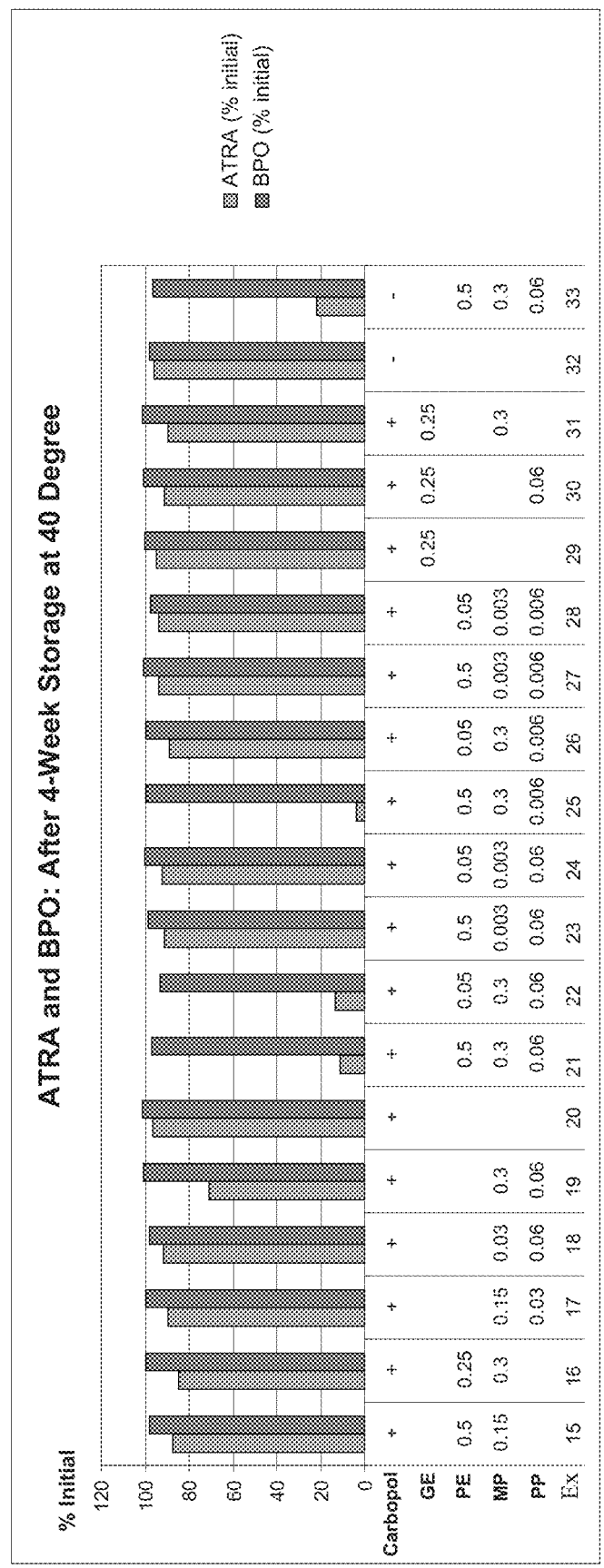
FIG. 1 is a plot illustrating ATRA and BPO levels for embodiments of various formulations after 4-week storage at 40° C.

Some embodiments provide a composition for topical application, where the composition contains: microcapsules having a core that comprises BPO and a shell that comprises an inorganic polymer, microcapsules having a core that comprises a retinoid and a shell that comprises an inorganic polymer, and a stabilizing agent. The stabilizing agent provides physical stabilization (e.g., bulk viscosity stabilization), chemical stabilization (e.g., active ingredient stabilization) and/or antimicrobial stabilization to the composition, as described in greater detail below. The composition can be in a variety of forms, including, but not limited to, an emulsion form, a cream form, an aqueous solution form, an oil form, an ointment form, a paste form, a gel form, a lotion form, and a suspension form. In some embodiments, the microcapsules having a core that comprises a retinoid or BPO can be in the form of an emulsion prior to formation of the composition. In further embodiments, these emulsions may be incorporated into a cream, gel, lotion, or other form providing the composition described above.

In some embodiments, the composition is in a gel form. It has been surprisingly discovered that a gel formulation comprising both benzoyl peroxide and retinoid in separated encapsulated forms was found to provide retinoid stability in the presence of a non-ionic polymeric dispersant and a thickening agent in the gel formulation. For example, an embodiment provides a composition for topical application, comprising: a plurality of first core-shell microcapsules comprising a first core that comprises benzoyl peroxide and a first shell that comprises a first inorganic polymer; a plurality of second core-shell microcapsules comprising a second core that comprises a retinoid and a second shell that comprises a second inorganic polymer; wherein said composition is in a gel form comprising at least one non-ionic polymeric dispersant and at least one thickening agent. As illustrated in the Examples below, in some embodiments the stability of the retinoid in a gel that contains a non-ionic polymeric dispersant (such as PVP) is surprisingly superior to that of the retinoid in the gel form that does not contain a non-ionic polymeric dispersant.

In other embodiments, the composition is in an emulsion form. It has been surprisingly found that in some embodiments, the retinoid in the emulsion is surprisingly stable. This finding is contrary to the expectations of the skilled artisan who would have instead expected the oil and surfactants in the emulsion to increase the rate of leaching of the retinoid out of its protective microcapsule. Surprisingly, no such increase in leaching was observed. For example, an embodiment provides a composition for topical application, comprising: a plurality of first core-shell microcapsules comprising a first core that comprises benzoyl peroxide and a first shell that comprises a first inorganic polymer; and a plurality of second core-shell microcapsules comprising a second core that comprises a retinoid and a second shell that comprises a second inorganic polymer; wherein said composition is an oil in water emulsion comprising a polyoxylstearate and a glycerylstearate, wherein the ratio of said polyoxylstearate to said glycerylstearate is in the range of 0.1:10 to 10:0.1. In an embodiment, the ratio of said polyoxylstearate to said glycerylstearate is in the range of 1:10 to 10:1. In another embodiment, the ratio of said polyoxylstearate to said glycerylstearate is in the range of 1:5 to 5:1. In another embodiment, the ratio of said polyoxylstearate to said glycerylstearate is in the range of 2:3 to 3:2. As illustrated in the Examples below, in some embodiments the stability of the retinoid in the emulsion form is surprisingly comparable to that of the retinoid in the gel form.

Various natural oils and synthetic oils (such as silicone oils) and mixtures thereof can be used as the oil component of the oil in water emulsion. Non-limiting examples of synthetic oils include paraffin oil, isopropyl myristate, caprylic/capric triglyceride, silicone oil (such as dimethicone and cyclomethicone) and mixtures thereof. Non-limiting examples of natural oils include squalane, almond oil, castor oil, olive oil, jojoba oil, sunflower oil, soybean oil, grape seed oil and mixtures thereof. Amounts of oil in the composition can be in the range of about 0.05% w/w to about 50% w/w. In an embodiment, amounts of oil in the composition can be in the range of about 0.5% w/w to about 20% w/w. In an embodiment, amounts of oil in the composition can be in the range of about 1% w/w to about 10% w/w.

Gel and emulsion forms of the composition can optionally contain other ingredients. For example, in an embodiment, the composition can contain at least one humectant. Non-limiting examples of humectants include water soluble humectants selected from the group consisting of propylene glycol, glycerin, polyethylene glycol-X, and mixtures thereof, where X indicates the average number of ethylene glycol units and is in the range of 200 to 10,000.

Microcapsules

As used herein, the term "microcapsule" refers to any micro- or nano-sized particle having a core-shell structure that is capable of encasing, encapsulating or entrapping compounds, including but not limited to active ingredients such as BPO and/or a retinoid (e.g., ATRA). In some embodiments, microcapsules are made by a sol-gel process, e.g., as generally described in WO 03/034979 and WO 2011/080741.

Core

As used herein, the term "core" refers to the inside part of a microcapsule comprising at least one active ingredient surrounded by a shell of the microcapsule. In some embodiments, the core can be solid at room temperature. In other embodiments, the core can be in a semi-solid phase at room temperature. In some embodiments, the core can be in the form of an emulsion, for example an oil-in-water emulsion. In some embodiments, the core can be in the form of oil solution. In some embodiments, the core can be in the form of an aqueous solution. In some embodiments, the core can be in the form of a dispersion.

Additional compound(s) can be present in the core. Non-limiting examples of the additional compounds that can be present in the core include phase changing materials (PCMs), carriers, excipients, antioxidants, pharmaceutically acceptable polymers, and salts. In some embodiments, the core comprises at least one phase changing material. As described elsewhere herein in greater detail, exemplary phase changing materials include, but are not limited to, natural and synthetic paraffins; $C_{10}$-$C_{100}$ (straight, branched, and cyclic) alkanes, alkenes and alkynes; $C_{10}$-$C_{100}$ aliphatic alcohols (e.g., fatty alcohols); fatty acids; carnauba wax; beeswax; and mixtures thereof. In some embodiments, the core comprises at least one antioxidant. Examples of antioxidants include, but are not limited to, butylated hydroxytoluene (BHT), butylated hydroxyanisole (BHA), vitamin E, vitamin E acetate, vitamin E palmitate, vitamin C, an ester of vitamin C, and one or more salts of vitamin C.

Shell

As used herein, the term "shell" refers to the part of a microcapsule that surrounds the core of the microcapsule. In some embodiments, the shell comprises an inorganic polymer (for example, a silica polymer). In some embodiments, the inorganic polymer can be prepared from a sol-gel precursor.

As used herein, the term "sol-gel precursor" refers to any metal or semi-metal organo-metallic monomer, or a prepolymer (which means several monomers polymerized together) thereof, which provide a glass or ceramic material by in-situ polymerization (an inorganic sol-gel polymerization process). In some embodiments, the sol-gel precursor can be a metal or semi-metal organo-metallic monomer. Examples of sol-gel precursor include, but are not limited to, a metal alkoxide monomer; a semi-metal alkoxide monomer; a metal ester monomer; a semi-metal ester monomer; a silazane monomer; a colloidal silica; a monomer of the formula $M(R)_n(P)_m$, where M can be a metallic or a semi-metallic element, R can be a hydrolyzable substituent, n can be an integer from 2 to 6, P can be a non polymerizable substituent, and m can be an integer from 0 to 6; and a partially hydrolyzed and partially condensed polymer thereof. Various metallic or semi metallic elements can be used in the sol-gel precursor, for example, Si, Ti, Zr, Al, and Zn. Examples of semi-metal alkoxide monomers include, but are not limited to, tetramethoxysilane (also known as tetramethyl orthosilicate or TMOS), tetraethoxysilane (also known as tetraethyl orthosilicate or TEOS), dimethyldimethoxysilane, methyltrimethoxysilane, diethyldimethoxysilane, and sodium silicate.

In some embodiments, the sol-gel precursor can be selected from a silicon alkoxide monomer; a silicon ester monomer; a monomer of the formula $Si(R)_n(P)_m$, wherein R can be a hydrolyzable substituent, n can be an integer from 2 to 4, P can be a non polymerizable substituent, and m can be an integer from 0 to 4; a partially hydrolyzed and partially condensed polymer of any of the above, and mixtures of any of the above. Non-limiting examples of silicon alkoxide monomer include tetramethoxy silane, tetraethoxy silane, and combinations thereof. Non-limiting examples of monomers of the formula $Si(R)n(P)m$ include methyl trimethoxysilane, dimethyl dimethoxysilane, and combinations thereof.

Active Ingredient

As used herein, the term "active ingredient" refers to a molecule or substance that can be used in medicine and/or cosmetics and which provides to the final product at least one desired property. Amounts of active ingredients in the compositions described herein are expressed in terms of weight percentage of the active ingredients in the composition based on the total weight of the composition, unless otherwise stated. Examples of active ingredients include but are not limited to BPO and retinoids (e.g., ATRA). The active ingredient can be present in the composition described herein in a variety of concentrations. For example, in certain embodiments, the amount of active ingredient in the composition can be about 0.001%, about 0.005%, about 0.01%, about 0.05%, about 0.1%, about 0.5%, about 1%, about 3%, about 5%, about 6%, about 7%, about 8%, about 9%, about 10%, about 15%, about 20%, or ranges between any two of these values, by weight, based on total weight of the composition. In some embodiments, the amount of active ingredient can be in the range of about 0.01% to about 1% by weight, based on total weight of the composition. In some embodiments, the amount of active ingredient can be in the range of about 1% to about 10% by weight, based on total weight of the composition. In particular embodiments, the amount of active ingredient can be about 3% by weight or about 6% by weight, based on total weight of the composition. In other embodiments, the amount of active ingredient can be about 0.1% by weight or about 0.05% by weight, based on total weight of the composition. In embodiments where multiple active ingredients are present, any combination of the foregoing amounts can be included.

The active ingredient can be a pharmaceutical agent, a cosmetic agent, a dermatological agent, an agrochemical agent, or any combination of the foregoing. In particular embodiments, the pharmaceutical agent, cosmetic agent, and/or dermatological agent can be an anti-acne agent. Examples of active ingredients include, but are not limited to, benzoyl peroxide (BPO) and a retinoid. Examples of retinoids include, but are not limited to, all-trans-retinol, all-trans-retinoic acid (also known as tretinoin or ATRA), retinol, retinal, isotretinoin, alitretinoin, etretinate (and its metabolite acitretin), tazarotene, bexarotene, and adapalene. In some embodiments, the active ingredient can be benzoyl peroxide. In some embodiments, the active ingredient can be a retinoid. In some embodiments, the active ingredient can be ATRA. In some embodiments, the retinoid can be present in the composition in an amount in the range of about 0.01% to about 1% by weight, based on total weight of the composition. In particular embodiments, the retinoid can be present in the composition in an amount in the range of about 0.05% by weight or about 0.1% by weight, based on the total weight of the composition. In some embodiments, benzoyl peroxide can be in the composition in an amount in the range of about 1% to about 10% by weight, based on total weight of the composition. In particular embodiments, the BPO can be present in the composition in an amount of about 6% by weight, based on the total weight of the composition. In other embodiments, the BPO can be present in the composition in an amount of about 3% by weight, based on the total weight of the composition.

In an embodiment, the amount of BPO can be about 6% by weight and the amount of retinoid can be about 0.1% by weight. An exemplary embodiment can be a composition in an emulsion form for topical application, comprising:

a plurality of first core-shell microcapsules comprising a first core that comprises benzoyl peroxide and a first shell that comprises a first silica polymer, the benzoyl peroxide being present in the composition in an initial amount of about 6% by weight, based on the total weight of the composition;

a plurality of second core-shell microcapsules comprising a second core that comprises all-trans retinoic acid (ATRA) and a second shell that comprises a second silica polymer, the ATRA being present in the composition in an initial amount of about 0.1% by weight, based on the total weight of the composition; and a stabilizing agent comprising (a) at least one non-ionic surfactant selected from the group consisting of polyoxyl 100 stearate and glycerol monostearate; and (b) at least one antimicrobial selected from the group consisting of methylparaben and imidazolidinyl urea;

wherein the stabilizing agent is present in an amount effective to:

(ia) maintain the amount of benzoyl peroxide at a level of at least about 5.4% by weight based on the total weight of the composition, as measured after storage of the composition at a storage condition selected from the group consisting of 40° C. for two months, 30° C. for three months, 25° C. for six months and 5° C. for two years;

(ib) maintain the amount of ATRA at a level of at least about 0.09% by weight based on the total weight of the composition, as measured after storage of the composition at a storage condition selected from the group consisting of 40° C. for two months, 30° C. for three months, 25° C. for six months and 5° C. for two years;

(ii) maintain the microbial count of the composition at a level that meets the criteria of USP 51, as measured by Antimicrobial Effectiveness Testing (AET) after storage of the composition at a storage condition of 40° C. for one month; and (iii) maintain the bulk viscosity of said composition at about one million cps or less and within a range of about 70% to about 130% of the initial bulk viscosity, as measured after storage of the composition at 25° C. for three months.

In another embodiment, the amount of BPO can be about 3% by weight and the amount of retinoid can be about 0.05% by weight. An exemplary embodiment can be a composition in an emulsion form for topical application, comprising:

a plurality of first core-shell microcapsules comprising a first core that comprises benzoyl peroxide and a first shell that comprises a first silica polymer, the benzoyl peroxide being present in the composition in an initial amount of about 3% by weight, based on the total weight of the composition;

a plurality of second core-shell microcapsules comprising a second core that comprises all-trans retinoic acid (ATRA)

and a second shell that comprises a second silica polymer, the ATRA being present in the composition in an initial amount of about 0.05% by weight, based on the total weight of the composition; and a stabilizing agent comprising (a) at least one non-ionic surfactant selected from the group consisting of polyoxyl 100 stearate and glycerol monostearate; and (b) at least one antimicrobial selected from the group consisting of methylparaben and imidazolidinyl urea;

wherein the stabilizing agent is present in an amount effective to:

(ia) maintain the amount of benzoyl peroxide at a level of at least about 2.7% by weight based on the total weight of the composition, as measured after storage of the composition at a storage condition selected from the group consisting of 40° C. for two months, 30° C. for three months, 25° C. for six months and 5° C. for two years;

(ib) maintain the amount of ATRA at a level of at least about 0.045% by weight based on the total weight of the composition, as measured after storage of the composition at a storage condition selected from the group consisting of 40° C. for two months, 30° C. for three months, 25° C. for six months and 5° C. for two years;

(ii) maintain the microbial count of the composition at a level that meets the criteria of USP 51, as measured by Antimicrobial Effectiveness Testing (AET) after storage of the composition at a storage condition of 40° C. for one month; and (iii) maintain the bulk viscosity of said composition at about one million cps or less and within a range of about 70% to about 130% of the initial bulk viscosity, as measured after storage of the composition at 25° C. for three months.

In some embodiments, the microcapsule can be configured to release at least one active ingredient encapsulated in the core by extraction. As used herein, the term "extraction" refers to an action or mechanism that induces the active ingredient to be released from its encapsulant upon topical application. In some embodiments, the extraction can be induced by a rubbing or spreading action. In some embodiments, the extraction can be induced via drying of the composition. In some embodiments, the extraction can be induced by contacting the microcapsules with a fat, a lipid, and/or an oil. In some embodiments, the fat, lipid, and/or oil are present in the skin. In some embodiments, the extraction can be induced by contacting the microcapsule with water, an electrolyte, a surfactant, a buffering agent, or any mixture thereof. In some embodiments, the water and electrolyte are present in a bodily fluid, such as sweat, or are present on the surface of the skin. In some embodiments, the electrolyte, the surfactant, the buffering agent, or the mixtures thereof are added to the composition prior to the topical application.

Stabilizing Agent

It has now been discovered that various compounds, referred to herein as a "stabilizing agent(s)", when used in an effective amount in a composition as described herein, can provide various types of stabilization, including active ingredient stabilization, bulk viscosity stabilization and/or antimicrobial stabilization. For example, in various embodiments an effective amount of a stabilizing agent in a composition as described herein can at least one of the following types or degrees of stabilization:

(a) maintain the amount of active ingredients (e.g., amount of BPO and the amount of retinoid) in the composition at a level that is at least about 90% of the initial amounts, as measured after storage of the composition at a storage condition selected from the group consisting of 40° C. for two months, 30° C. for three months, 25° C. for six months and 5° C. for two years;

(b) maintain the amount of the amount of active ingredients (e.g., amount of BPO and the amount of retinoid in the composition at a level that is at least about 97% of the initial amounts, as measured after storage of the composition at a storage condition of 5° C. for two years;

(c) maintain the microbial count of the composition at a level that meets the criteria of USP 51, as measured by Antimicrobial Effectiveness Testing (AET) after storage of the composition at a storage condition of 40° C. for one month;

(d) maintain the microbial count of the composition at a level that meets the criteria of USP 61, as measured by Microbial Limits Testing (MLT) after storage of the composition at a storage condition of 25° C. for six months;

(e) maintain the bulk viscosity of the composition at a level selected from the group consisting of about one million cps or less, about 500,000 or less, and about 300,000 or less, as measured after storage of the composition at 25° C. for three months;

(f) maintain the bulk viscosity of the composition at a level selected from the group consisting of about 60,000 cps or more, about 80,000 or more, and about 120,000 or more, as measured after storage of the composition at 25° C. for three months;

(g) maintain the bulk viscosity of the composition at a level within a range of about 70% to about 130% of the initial bulk viscosity, as measured after storage of the composition at 25° C. for three months.

A stabilizer can be a single compound or a mixture of compounds. In some embodiments a stabilizer can provide a single type of stability, such as active ingredient stabilization, bulk viscosity stabilization or antimicrobial stabilization, including but not limited to one of stabilization types (a) through (g) above. In other embodiments a stabilizer can provide two or more types of stability, such as two or more of active ingredient stabilization, bulk viscosity stabilization or antimicrobial stabilization, including but not limited to a plurality of stabilization types (a) through (g) above. In some embodiments an effective amount of a stabilizer provides a particular type or types of stability, and a different amount provides a different type or types of stability. Routine experimentation guided by the teachings provided herein can be used to identify compounds and mixtures thereof that provide one or more types of stability, and thus all combinations of effective stabilizing agents and types of stabilization are encompassed by the descriptions provided herein.

Various compounds can be used as a stabilizing agent, including non-ionic surfactants, water-soluble non-ionic polymers (including non-ionic polymeric dispersants and water-soluble non-ionic polymers), antimicrobials, thickening agents (including ionic and non-ionic thickening agents) and mixtures thereof.

Non-limiting examples of non-ionic surfactants useful as stabilizing agents include but are not limited to polyoxylstearates and glycerylstearates. Non-limiting examples of suitable polyoxylstearates include polyoxyl-8 stearate, polyoxyl-20 stearate, polyoxyl-40 stearate, polyoxyl-100 stearate, and mixtures thereof. Non-limiting examples of suitable glycerylstearates include glyceryl mono-stearate, glyceryl di-stearate, and mixtures thereof. Amounts of polyoxylstearates and/or glycerylstearates in the composition (such as in an emulsion composition), can be in the range of about 0.1% w/w to about 30% w/w. In an embodiment, amounts of polyoxylstearates and/or glycerylstearates in the composition can be in the range of about 0.5% w/w to about 10% w/w. In an embodiment, amounts of polyoxylstearates and/or glycerylstearates in the composition can be in the range of about 1% w/w to about 5% w/w.

Non-limiting examples of water-soluble non-ionic polymers include non-ionic polymeric dispersants such as (but not limited to) polyvinyl pyrrolidone (PVP), polyvinyl pyrrolidone-co-vinyl acetate, polyamide, polyurethane, polyurea, and mixtures thereof. Amounts of water-soluble non-ionic polymers (such as polymeric dispersants) in the composition can be in the range of about 0.05% w/w to about 20% w/w. In an embodiment, amounts of water-soluble non-ionic polymers in the composition can be in the range of about 0.1% w/w to about 10% w/w. In an embodiment, amounts of water-soluble non-ionic polymers in the composition can be in the range of about 0.5% w/w to about 5% w/w.

Non-limiting examples of thickening agents include hydroxy propyl cellulose (HPC), hydroxyl ethyl cellulose (HEC), hydroxyl methyl cellulose (HMC), polyacrylic acid homopolymer, polyacrylic acid copolymer, silica and its derivatives, xanthan gum, arabic gum, polyvinyl alcohol, fatty alcohols, veegum, laponite, clay, and mixtures thereof. Polyacrylic acid polymers and copolymers may be referred to herein as carbomers, which are commercially available under various tradenames such as CARBOMER 934, CARBOMER 941, CARBOMER 934P, CARBOPOL 910, CARBOPOL 934, CARBOPOL 941, etc. Amounts of thickening agents in the composition can be in the range of about 0.01% w/w to about 10% w/w. In an embodiment, amounts of thickening agents in the composition can be in the range of about 0.05% w/w to about 5% w/w. In an embodiment, amounts of thickening agents in the composition can be in the range of about 0.1% w/w to about 2% w/w. In an embodiment of a composition that contains both a polymeric dispersant and a thickening agent, the polymeric dispersant can be different from the thickening agent.

In an embodiment, the stabilizing agent is polyvinylpyrrolidone (PVP), polyoxyl 100 stearate, glycerol monostearate, methylparaben, propylparaben, phenoxyethanol, imidazolidinyl urea, or a mixture thereof. Other compounds useful as stabilizing agents can be identified by routine experimentation guided by the teachings provided herein. With respect to compositions that contain BPO as an active ingredient, the BPO is not considered to be a stabilizing agent even if it exhibits antimicrobial properties. Thus, reference herein to a stabilizing agent or antimicrobial in a composition that contains BPO as an active ingredient will be understood by those skilled in the art as a reference to a second antimicrobial that is not BPO.

The stabilizing agent can be a single compound or a mixture of compounds and can provide more that one type of stability, e.g., active ingredient stabilization, bulk viscosity stabilization and/or antimicrobial stabilization. For example, in an embodiment, the stabilizing agent can be polyoxyl 100 stearate, glycerol monostearate, or a mixture thereof, in an amount that provides active ingredient stabilization and bulk viscosity stabilization as described herein. In another embodiment, the stabilizing agent can be an antimicrobial, including but not limited to methylparaben, propylparaben, phenoxyethanol, imidazolidinyl urea, or a mixture thereof, in an amount that provides active ingredient stabilization and antimicrobial stabilization as described herein. In another embodiment, the stabilizing agent can include polyoxyl 100 stearate, glycerol monostearate, or a mixture thereof, and further include methylparaben, propylparaben, phenoxyethanol, imidazolidinyl urea, or a mixture thereof, in an amount that provides active ingredient stabilization, bulk viscosity stabilization and antimicrobial stabilization as described herein.

In some embodiments, the stabilizing agent can be present in an amount effective to maintain the viscosity of the composition. In some embodiments, the viscosity of the composition can be maintained such that the change in viscosity of the composition, as measured after manufacture followed by three months storage at about 25° C. can be less than about 30%. In some embodiments, the viscosity of the composition can be maintained such that the change in viscosity of the composition, as measured after manufacture followed by three months storage at about 25° C. can be less than about 20%. In some embodiments, the viscosity of the composition can be maintained such that the change in viscosity of the composition, as measured after manufacture followed by three months storage at about 5° C., can be less than about 30%.

In some embodiments, the stabilizing agent can be present in an amount effective to inhibit the degradation of at least one active ingredient in the composition. In some embodiments, the active ingredient can be a retinoid. In some embodiments, the active ingredient can be all-trans retinoic acid (ATRA). In some embodiments, the amount of degradation of ATRA, as measured after manufacture followed by three months storage at about 25° C. can be less than about 10%. In some embodiments, the amount of degradation of ATRA, as measured after manufacture followed by three months storage at about 25° C. can be less than about 5%. In some embodiments, the amount of degradation of ATRA, as measured after manufacture followed by three months storage at about 5° C. can be less than about 10%. In some embodiments, the amount of degradation of ATRA, as measured after manufacture followed by three months storage at about 5° C. can be less than about 5%.

Those skilled in the art appreciate that the value obtained for a bulk viscosity measurement depends on the instrument of measurement, spindle used, speed of the instrument, and temperature of measurement. The bulk viscosity measurements referred to herein are measured using a Brookfield LVDV-II+Pro viscometer equipped with a small sample adaptor, spindle #63 (LV3) or spindle #SC4-25 at 1 rpm and at temperature of 30° C.±0.5° C. Antimicrobial stability can be measured in accordance with the criteria of USP 51, as measured by Antimicrobial Effectiveness Testing (AET) after storage of the composition at a storage condition of 40° C. for one month, and/or antimicrobial stability can be measured in accordance with the criteria of USP 61, as measured by Microbial Limits Testing (MLT) after storage of the composition at a storage condition of 25° C. for six months.

Phase Changing Material

As used herein, the term "phase changing material" (PCM) refers to any substance capable of changing its state of matter (phase), or at least its viscosity, in accordance with the temperature it is exposed to. PCMs typically have a high heat of fusion which enables them to melt and solidify at certain temperatures, and are capable of storing and releasing large amounts of energy. Heat is absorbed or released when the PCM material changes from solid to liquid and vice versa. When a PCM reaches the temperature at which it changes phase or viscosity (for example its melting temperature), it absorbs large amounts of heat but is maintained at almost constant temperature. The PCM continues to absorb heat without a significant rise in temperature until all the material is transformed to the liquid phase. When the ambient temperature around the resulting liquid material falls, the PCM solidifies, releasing its stored latent heat.

As described herein, a PCM is typically non-reactive with the active ingredient encapsulated in the microcapsule, the emulsion formed, and the shell of the microcapsule described herein. In some embodiments, the PCM can be an organic material. Examples of PCMs include, but are not limited to, natural or synthetic paraffins (typically compounds having a molecular formula of $C_nH_{2n+2}$, (n=10-100)), $C_{10}$-$C_{100}$ straight, branched, and cyclic alkanes, $C_{10}$-$C_{100}$ straight, branched, and cyclic alkenes (compounds having the noted number of carbons and at least one double bond), straight and branched $C_{10}$-$C_{100}$ alkynes (compounds having the noted number of carbons and at least one triple bond), straight and branched aliphatic alcohols (typically compounds having a molecular formula of $CH_3(CH_2)_nOH$ or branched versions thereof, wherein n=10-100) and fatty acids (typically compounds having a molecular formula of $CH_3(CH_2)_{2n}COOH$ and branched versions thereof, wherein n=10-100), or any combinations thereof.

In some embodiments, the PCM can be a natural or a synthetic paraffin. In some embodiments, the PCM can be a $C_{10}$-$C_{100}$ aliphatic alcohol (for example, $C_{10}$, $C_{20}$, $C_{30}$, $C_{40}$, $C_{50}$, $C_{60}$, $C_{70}$, $C_{80}$, $C_{90}$ to $C_{100}$ aliphatic alcohol). In other embodiments, the PCM can be a $C_{10}$-$C_{100}$ aliphatic fatty acid (for example, $C_{10}$, $C_{20}$, $C_{30}$, $C_{40}$, $C_{50}$, $C_{60}$, $C_{70}$, $C_{80}$, $C_{90}$ to $C_{100}$ aliphatic fatty acids).

In an embodiment, the PCM can be at least one fatty alcohol. Non-limiting examples of fatty alcohols include octyl alcohol, 2-ethyl hexanol, nonyl alcohol, decyl alcohol, undecanol, dodecyl alcohol, tridecyl alcohol, tetradecyl alcohol, pentadecyl alcohol, cetyl alcohol, palmitoleyl alcohol, heptadecyl alcohol, cetostearyl alcohol, stearyl alcohol, isostearyl alcohol, elaidyl alcohol, oleyl alcohol, linoleyl alcohol, elaidolinolenyl alcohol, ricinoleyl alcohol, nonadecyl alcohol, arachidyl alcohol, heneicosyl alcohol, behenyl alcohol, erucyl alcohol, lignoceryl alcohol, ceryl alcohol, montanyl alcohol, cluytyl alcohol, myricyl alcohol, melissyl alcohol, geddyl alcohol, cetearyl alcohol and mixtures thereof. Amounts of fatty alcohol in the composition can be in the range of about 0.2% w/w to about 50% w/w. In an embodiment, amounts of fatty alcohol in the composition can be in the range of about 1% w/w to about 20% w/w. In an embodiment, amounts of fatty alcohol in the composition can be in the range of about 3% w/w to about 10% w/w.

Exemplary PCMs include, but are not limited to: Carnauba wax (m.p. 82-86° C.), Beeswax pure (m.p. 61-65° C.), Beeswax white pure, (m.p. 61-65° C.), Beeswax bleached technical (m.p. 61-65° C.), Montan wax bleached (m.p. 80-86° C.), Montan wax bleached, partially saponified (m.p. 99-105° C.), Montanic acid (m.p. 81-87° C.), Hydrocarbon wax synthetic (m.p. 106-114° C.), Microcrystalline wax (m.p. 89-95° C.), Microcrystalline wax (m.p. 76-82° C.), Hardwax partially saponified (m.p. 104-109° C.), Beeswax yellow (m.p. 61-66° C.), Polishing Wax (m.p. 78-84° C.), Castor wax (m.p. 83-89° C.), Microwax (m.p. 89-95° C.), Microwax (m.p. 80-86° C.), Microwax (m.p. 76-82° C.), Ozokerite (m.p. 72-79° C.), Microcrystalline wax, plastic (m.p. 76-82° C.), Microcrystalline wax, soft (m.p. 74-80° C.), Wax blend (m.p. 62-68° C.), Polyolefin wax (m.p. 65-75° C.), Lanolin, Shellac, Bayberry wax (m.p. 45° C.), Candelilla wax (m.p. 67-79° C.), Ouricury wax, Rice bran wax (m.p. 77-86° C.), Soy candle (wax), Paraffin (m.p. 47-64° C.), Chinese wax, and any combinations thereof.

In some embodiments, the core comprises at least one PCM. In some embodiments, the PCM can be a natural paraffin, a synthetic paraffin, an aliphatic alcohol, a fatty acid, an ester of an aliphatic alcohol, an ester of a fatty acid, or combinations thereof. In some embodiments, the ester of a fatty acid comprises natural or synthetic beeswax.

In some embodiments, the PCM can be in the core of obtained microcapsules and not incorporated in any part of the shell of the microcapsules described herein.

Compositions for Topical Application

As used herein, the term "topical" application refers to an application onto the skin, hair, ears, and/or mucous membranes.

Some embodiments disclosed herein provide a composition for topical application, wherein the composition comprises: a plurality of first microcapsules having a core that comprises benzoyl peroxide and a shell that comprises an inorganic polymer, a plurality of second microcapsules having a core that comprises a retinoid and a shell that comprises an inorganic polymer, and a stabilizing agent.

Some embodiments disclosed herein provide a composition in a gel form for topical application, where the composition comprises: a plurality of first microcapsules having a core that comprises benzoyl peroxide and a shell that comprises a first silica polymer; a plurality of second microcapsules having a core that comprises all-trans retinoic acid (ATRA) and a shell that comprises a second silica polymer; and at least one non-ionic polymer in an amount effective to provide viscosity stabilization and/or degradation stabilization. In some embodiments, the viscosity stabilization means that the viscosity of the composition can be maintained such that the change in viscosity of the composition, as measured after manufacture followed by three months storage at about 25° C. can be less than about 30%. In some embodiments, the degradation stabilization means that the amount of degradation of the ATRA, as measured after manufacture followed by three months storage at about 25° C. can be less than about 10%.

In some embodiments, the non-ionic polymer can be present in an amount effective to provide viscosity stabilization. In some embodiments, the viscosity stabilization can be effective to maintain the viscosity of the composition at more than about 20,000 cps, about 25,000 cps, about 30,000 cps, about 35,000 cps, about 40,000 cps, about 45,000 cps, or about 50,000 cps as measured after manufacture followed by 3 months storage at a storage temperature. The storage temperature can be about 5° C. or about 25° C. In some embodiments, the non-ionic polymer can be present in an amount effective to provide degradation stabilization. In some embodiments, the non-ionic polymer can be present in an amount such that the amount of degradation of ATRA can be less than about 10%, 8%, or 5%. In some embodiments, the non-ionic polymer can be polyvinylpyrrolidone.

In certain embodiments, the non-ionic polymer can be present in an amount effective to provide the viscosity stabilization and degradation stabilization. Other non-ionic polymers and effective amounts thereof that provide the viscosity stabilization and/or the degradation stabilization may be identified by those skilled in the art using routine experimentation guided by the teachings provided herein. Non-limiting examples of suitable non-ionic polymers include polyvinyl pyrrolidone (PVP), polyvinyl pyrrolidone-co-vinyl acetate, polyamide, polyurethane, polyurea, and mixtures thereof.

Some embodiments provide a composition in an emulsion form for topical application, where the composition comprises: a plurality of first microcapsules having a core that comprises benzoyl peroxide and a shell that comprises a silica polymer; a plurality of second microcapsules having a core that comprises all-trans retinoic acid (ATRA) and a shell that comprises a silica polymer; and at least one non-ionic surfactant in an amount effective to provide viscosity stabilization and/or degradation stabilization.

In some embodiments, the non-ionic surfactant can be present in an amount effective to provide viscosity stabilization. In some embodiments, the viscosity stabilization can be effective to maintain the viscosity of the composition at more than about 60,000 cps, 70,000 cps, 80,000 cps, 90,000 cps, 100,000 cps, 110,000 cps, 120,000 cps, 130,000 cps, 140,000 cps, 150,000 cps, 160,000 cps, or 170,000 cps as measured after manufacture followed by three months storage at a storage temperature. The storage temperature can be about 5° C. or about 25° C. In some embodiments, the non-ionic surfactant can be present in an amount effective to provide degradation stabilization. In some embodiments, the non-ionic surfactant can be present in an amount such that the amount of degradation of ATRA can be less than about 10%, 8%, or 5%.

In some embodiments, the non-ionic surfactant can be present in an amount effective to provide the viscosity stabilization and the degradation stabilization. Non-limiting examples of non-ionic surfactants include polyoxylstearates and glycerylstearates. Non-limiting examples of polyoxylstearates include Polyoxyl-8 stearate, Polyoxyl-20 stearate, Polyoxyl-40 stearate, and Polyoxyl-100 stearate. Non-limiting examples of glycerylstearates include glyceryl mono-stearate, glyceryl di-stearate, and mixtures thereof. Other non-ionic surfactants and effective amounts thereof that provide the viscosity stabilization and/or the degradation stabilization may be identified by those skilled in the art using routine experimentation guided by the teachings provided herein. In some embodiments, the non-ionic surfactant comprises a combination of polyoxyl 100 stearate and glycerol monostearate.

Various stabilizations described herein, for example, the viscosity stabilization and/or the degradation stabilization, may be effective for a storage time beyond 3 months at a storage temperature. For example, in some embodiments, the various viscosity stabilizations and/or the degradation stabilizations described herein are effective for a storage time of about 6 months, about 9 months, about 12 months, about 15 months, about 18 months, or about 24 months. In some embodiments, the storage temperature can be about 5° C., or about 25° C.

In another aspect, the present disclosure provides methods of preparing a composition comprising microcapsules disclosed herein. Those skilled in the art will appreciate the manner in which the working examples set forth below provide a specific description of how to make particular compositions and components thereof. Those skilled in the art will also appreciate the manner in which the specific working examples can be generalized and adapted to produce the other compositions described herein and components thereof.

In yet another aspect, the present disclosure provides a method for treating a surface condition (e.g., a skin disease or disorder) in a subject in need thereof, comprising topically administering to the subject an effective amount of a composition as described herein. Non-limiting examples of surface conditions that can be treated by topical application of effective amounts of the compositions described herein include acne, rosecea, psoriasis, photoaged skin, hyperpigmented skin, mucosal infected areas, inflamed dermatitis, and combinations thereof. In this context, terms such as "treat," "treating," "treatment," etc. include inhibiting the surface condition (e.g., by arresting its development), relieving the surface condition (e.g., causing regression) and/or relieving one or more conditions caused by the surface condition (e.g., reducing one or more symptoms). Effective amounts of the compositions described herein for treating various surface conditions can be determined by those skilled in the art in the usual manner, e.g., by clinical trials, with appropriate adjustments by skilled clinicians in individual cases.

In yet another aspect, the present disclosure provides a packaged product, comprising a sealable container and a composition as described herein that is contained within the sealable container. The sealable container can have many different configurations, e.g., including but not limited to the various types of containers that are used for packaging cream, gel and ointment products for consumer use. Non-limiting examples of suitable sealable containers include pump-type bottles, nozzle-type bottles, tubes, sachets, packets, and various other configurations known to those skilled in the art.

An embodiment provides a composition for topical application, comprising:

a plurality of first core-shell microcapsules comprising a first core that comprises benzoyl peroxide and a first shell that comprises a first inorganic polymer; and a plurality of second core-shell microcapsules comprising a second core that comprises a retinoid and a second shell that comprises a second inorganic polymer;

wherein said composition is an oil in water emulsion comprising a polyoxylstearate and a glycerylstearate wherein the ratio of said polyoxylstearate to said glycerylstearate is in the range of 0.1:10 to 10:0.1.

In various embodiments, said polyoxylstearate is selected from the group consisting of Polyoxyl-8 stearate, Polyoxyl-20 stearate, Polyoxyl-40 stearate, and Polyoxyl-100 stearate.

In various embodiments, said glycerylstearate is selected from the group consisting of glyceryl mono-stearate, glyceryl di-stearate and mixtures thereof.

In various embodiments, the amount of said polyoxylstearate in said composition is in the range of about 0.1% w/w to about 30% w/w.

In various embodiments, the amount of said glycerylstearate in said composition is in the range of about 0.1% w/w to about 30% w/w.

In various embodiments, said composition further comprises at least one fatty alcohol.

In various embodiments, said at least one fatty alcohol is selected from the group consisting of octyl alcohol, 2-ethyl hexanol, nonyl alcohol, decyl alcohol, undecanol, dodecyl alcohol, tridecyl alcohol, tetradecyl alcohol, pentadecyl alcohol, cetyl alcohol, palmitoleyl alcohol, heptadecyl alcohol, cetostearyl alcohol, stearyl alcohol, isostearyl alcohol, elaidyl alcohol, oleyl alcohol, linoleyl alcohol, elaidolinolenyl alcohol, ricinoleyl alcohol, nonadecyl alcohol, arachidyl alcohol, heneicosyl alcohol, behenyl alcohol, erucyl alcohol, lignoceryl alcohol, ceryl alcohol, montanyl alcohol, cluytyl alcohol, myricyl alcohol, melissyl alcohol, geddyl alcohol, cetearyl alcohol and mixtures thereof.

In various embodiments, the amount of said at least one fatty alcohol in said composition is in the range of about 0.2% w/w to about 50% w/w.

In various embodiments, said composition further comprises a polyacrylic acid homopolymer or copolymer.

In various embodiments, said oil in said oil in water emulsion is selected from the group consisting of paraffin oil, isopropyl myristate, caprylic/capric triglyceride, squalane, squalene, almond oil, castor oil, olive oil, jojoba oil, sunflower oil, soybean oil, grape seed oil, dimethicone, cyclomethicone and mixtures thereof.

In various embodiments, said oil in present in the composition in an amount in the range of about 0.05% w/w to about 50% w/w.

In various embodiments, said water in said oil in water emulsion further comprises at least one water soluble humectant.

In various embodiments, said at least one water soluble humectant is selected from the group consisting of propylene glycol, glycerin, and polyethylene glycol-X, where X is in the range of 200 to 10,000.

Another embodiment provides a composition for topical application, comprising:

a plurality of first core-shell microcapsules comprising a first core that comprises benzoyl peroxide and a first shell that comprises a first inorganic polymer; and a plurality of second core-shell microcapsules comprising a second core that comprises a retinoid and a second shell that comprises a second inorganic polymer;

wherein said composition is in a gel form comprising at least one non-ionic polymeric dispersant and at least one thickening agent.

In various embodiments, said at least one non-ionic polymeric dispersant is selected from the group consisting of poly vinyl pyrrolidone (PVP), poly vinyl pyrrolidone-co-vinyl acetate, polyamide, polyurethane, polyurea and mixtures thereof.

In various embodiments, said at least one thickening agent is selected from the group consisting of hydroxy propyl cellulose (HPC), hydroxyl ethyl cellulose (HEC), hydroxyl methyl cellulose (HMC), polyacrylic acid homopolymer, polyacrylic acid copolymer, fatty alcohol, silica and its derivatives, xanthan gum, arabic gum, poly vinyl alcohol, veegum, laponite, clay, and mixtures thereof.

In various embodiments, said at least one thickening agent is a non-ionic agent.

In various embodiments, said at least one thickening agent is an ionic agent.

In various embodiments, said at least one thickening agent is present in the composition in an amount in the range of about 0.01% w/w to about 10% w/w.

In various embodiments, said composition further comprises glycerin.

In various embodiments, said non-ionic polymeric dispersant is present in the composition in an amount in the range of about 0.05% w/w to about 20% w/w.

In various embodiments, said composition further comprises at least one antimicrobial agent.

In various embodiments, said at least one antimicrobial agent is selected from the group consisting of methylparaben, propylparaben, phenoxyethanol, imidazolidinyl urea and mixtures thereof.

In various embodiments, at least one of said first core-shell microcapsules and said second core-shell microcapsules further comprise at least one phase changing material selected from the group consisting of a natural paraffin, a synthetic paraffin, an aliphatic alcohol, and a fatty acid.

In various embodiments, said first inorganic polymer is different from said second inorganic polymer.

In various embodiments, said first inorganic polymer and said second inorganic polymer are the same.

In various embodiments, said first inorganic polymer and said second inorganic polymer are each independently prepared from a sol-gel precursor selected from the group consisting of a metal alkoxide monomer, a semi-metal alkoxide monomer, a metal ester monomer, a semi-metal ester monomer, a silazane monomer, a colloidal silica, a monomer of the formula M(R)n(P)m, wherein M is a metallic or a semi-metallic element, R is a hydrolyzable substituent, n is an integer from 2 to 6, P is a non polymerizable substituent and m is an integer from 0 to 6, and a partially hydrolyzed and partially condensed polymer thereof.

In various embodiments, said semi-metal alkoxide monomer is selected from the group consisting of tetramethoxysilane, tetraethoxysilane, dimethyl dimethoxysilane, methyl trimethoxysilane, dimethyl dimethoxysilane, and sodium silicate.

In various embodiments, the amount of said benzoyl peroxide is in the range of about 1% to about 10% by weight, based on total weight of said composition.

In various embodiments, the amount of said retinoid is in the range of about 0.01% to about 1% by weight, based on total weight of said composition.

In various embodiments, said composition further comprises at least one antioxidant.

In various embodiments, said at least one antioxidant is selected from the group consisting of butylated hydroxytoluene (BHT), butylated hydroxyanisole, vitamin E, vitamin E acetate, vitamin E palmitate, vitamin C, an ester of vitamin C, and a salt of vitamin C or any combinations thereof.

In various embodiments, said at least one antioxidant is incorporated into the core of said second core-shell microcapsule.

An embodiment provides a composition for topical application, comprising:

a plurality of first core-shell microcapsules comprising a first core that comprises benzoyl peroxide and a first shell that comprises a first inorganic polymer;

a plurality of second core-shell microcapsules comprising a second core that comprises a retinoid and a second shell that comprises a second inorganic polymer; and an amount of a stabilizing agent that is effective to:

(i) maintain the amount of benzoyl peroxide and the amount of retinoid in the composition at a level that is at least about 90% of the initial amounts, as measured after storage of the composition at a storage condition of 30° C. for three months; and (ii) maintain the microbial count of the composition at a level that meets the criteria of USP 51, as measured by Antimicrobial Effectiveness Testing (AET) after storage of the composition at a storage condition of 40° C. for one month.

In various embodiments, said stabilizing agent is selected from the group consisting of polyvinylpyrrolidone, polyoxyl 100 stearate, glycerol monostearate, methylparaben, propylparaben, phenoxyethanol, imidazolidinyl urea and mixtures thereof.

In various embodiments, said stabilizing agent is further effective to (iii) maintain the bulk viscosity of said composition at about one million cps or less and within a range of about 70% to about 130% of the initial bulk viscosity, as measured after storage of the composition at 25° C. for three months.

In various embodiments, the bulk viscosity of said composition is maintained at about 500,000 cps or less.

In various embodiments, said stabilizing agent is further effective to (iv) maintain the microbial count of the composition at a level that meets the criteria of USP 61, as measured by Microbial Limits Testing (MLT) after storage of the composition at a storage condition of 25° C. for six months.

In various embodiments, said stabilizing agent is present in an amount effective to maintain the amount of benzoyl peroxide and the amount of retinoid in the composition at a level of at least about 90% of the initial amounts, as measured after storage of the composition at a storage condition selected from the group consisting of 40° C. for two months, 25° C. for six months and 5° C. for two years.

In various embodiments, said stabilizing agent is present in an amount effective to maintain the amount of benzoyl peroxide and the amount of retinoid in the composition at a level of at least about 97% of the initial amounts, as measured after storage of the composition at a storage condition of 5° C. for two years.

In various embodiments, said stabilizing agent is a mixture comprising at least two selected from the group consisting of polyvinylpyrrolidone, polyoxyl 100 stearate, glycerol monostearate, methylparaben, propylparaben, phenoxyethanol, and imidazolidinyl urea.

In various embodiments, said second core further comprises at least one phase changing material selected from the group consisting of a natural paraffin, a synthetic paraffin, an aliphatic alcohol, and a fatty acid.

In various embodiments, said first inorganic polymer is different from said second inorganic polymer.

In various embodiments, said first inorganic polymer and said second inorganic polymer are the same.

In various embodiments, said first inorganic polymer and said second inorganic polymer are each independently prepared from a sol-gel precursor selected from the group consisting of a metal alkoxide monomer, a semi-metal alkoxide monomer, a metal ester monomer, a semi-metal ester monomer, a silazane monomer, a colloidal silica, a monomer of the formula $M(R)_n(P)_m$, wherein M is a metallic or a semi-metallic element, R is a hydrolyzable substituent, n is an integer from 2 to 6, P is a non polymerizable substituent and m is an integer from 0 to 6, and a partially hydrolyzed and partially condensed polymer thereof.

In various embodiments, said semi-metal alkoxide monomer is selected from the group consisting of tetramethoxysilane, tetraethoxysilane, dimethyl dimethoxysilane, methyl trimethoxysilane, dimethyl dimethoxysilane, and sodium silicate.

In various embodiments, the amount of said benzoyl peroxide is in the range of about 1% to about 10% by weight, based on total weight of said composition.

In various embodiments, the amount of said retinoid is in the range of about 0.01% to about 1% by weight, based on total weight of said composition.

In various embodiments, said composition is in a form selected from the group consisting of an emulsion, a cream, an aqueous solution, an oil, an ointment, a paste, a gel, a lotion, and a suspension.

In various embodiments, said microcapsules are configured to release at least one of the benzoyl peroxide and the retinoid by extraction.

In various embodiments, said second core further comprises an antioxidant.

In various embodiments, said antioxidant is selected from the group consisting of butylated hydroxytoluene (BHT), butylated hydroxyanisole, vitamin E, vitamin E acetate, vitamin E palmitate, vitamin C, an ester of vitamin C, and a salt of vitamin C.

Another embodiment provides a composition in a gel form for topical application, comprising:

a plurality of first core-shell microcapsules comprising a first core that comprises benzoyl peroxide and a first shell that comprises a first silica polymer;

a plurality of second core-shell microcapsules comprising a second core that comprises all-trans retinoic acid (ATRA) and a second shell that comprises a second silica polymer; and at least one non-ionic polymer in an amount effective to provide at least one stabilization selected from the group consisting of (i) viscosity stabilization whereby the viscosity of said composition is maintained such that the change in viscosity of said composition, as measured after manufacture followed by three months storage at 25° C., is less than about 30%, and (ii) degradation stabilization whereby the amount of degradation of said ATRA, as measured after manufacture followed by three months storage at 25° C., is less than about 10%.

In various embodiments, said non-ionic polymer is present in an amount effective to provide said viscosity stabilization.

In various embodiments, said viscosity stabilization is effective to maintain the viscosity of said composition at more than about 25,000 cps as measured after manufacture followed by three months storage at 25° C.

In various embodiments, said non-ionic polymer is present in an amount effective to provide said degradation stabilization.

In various embodiments, the amount of degradation of said ATRA is less than about 5%.

In various embodiments, said non-ionic polymer is present in an amount effective to provide said viscosity stabilization and said degradation stabilization.

In various embodiments, said non-ionic polymer is polyvinylpyrrolidone.

In various embodiments, said second core further comprises at least one phase changing material selected from the group consisting of a natural paraffin, a synthetic paraffin, an aliphatic alcohol, a fatty acid, an ester of an aliphatic alcohol, and an ester of a fatty acid.

In various embodiments, said ester of a fatty acid comprises a beeswax.

In various embodiments, said second core further comprises an antioxidant.

In various embodiments, said antioxidant is selected from the group consisting of butylated hydroxytoluene (BHT), butylated hydroxyanisole, vitamin E, vitamin E acetate, vitamin E palmitate, vitamin C, an ester of vitamin C, and a salt of vitamin C.

In various embodiments, said first inorganic polymer is different from said second inorganic polymer.

In various embodiments, said first inorganic polymer and said second inorganic polymer are the same.

In various embodiments, said first silica polymer and said second silica polymer are each independently prepared from a sol-gel precursor selected from the group consisting of tetramethoxysilane, tetraethoxysilane, and sodium silicate.

In various embodiments, the initial amount of said benzoyl peroxide is in the range of about 1% to about 10% by weight, based on the total weight of said composition.

In various embodiments, the initial amount of said benzoyl peroxide is about 6% by weight, based on the total weight of said composition.

In various embodiments, the initial amount of said benzoyl peroxide is about 3% by weight, based on the total weight of said composition.

In various embodiments, the initial amount of said ATRA is in the range of about 0.01% to about 1% by weight, based on the total weight of said composition.

In various embodiments, the initial amount of said ATRA is about 0.1% by weight, based on the total weight of said composition.

In various embodiments, the initial amount of said ATRA is about 0.05% by weight, based on the total weight of said composition.

Another embodiment provides a composition in an emulsion form for topical application, comprising:

a plurality of first core-shell microcapsules comprising a first core that comprises benzoyl peroxide and a first shell that comprises a first silica polymer;

a plurality of second core-shell microcapsules comprising a second core that comprises all-trans retinoic acid (ATRA) and a second shell that comprises a second silica polymer; and a stabilizing agent comprising at least one non-ionic surfactant and at least one antimicrobial in amounts effective to:

(i) maintain the amount of benzoyl peroxide and the amount of retinoid in the composition at a level that is at least about 90% of the initial amounts, as measured after storage of the composition at a storage condition selected from the group consisting of 40° C. for two months, 30° C. for three months, 25° C. for six months and 5° C. for two years; and (ii) maintain the microbial count of the composition at a level that meets the criteria of USP 51, as measured by Antimicrobial Effectiveness Testing (AET) after storage of the composition at a storage condition of 40° C. for one month.

In various embodiments, said stabilizing agent is further effective to (iii) maintain the bulk viscosity of said composition at about three million cps or less and within a range of about 70% to about 130% of the initial bulk viscosity, as measured after storage of the composition at 25° C. for three months.

In various embodiments, said stabilizing agent is effective to maintain the bulk viscosity of said composition in the range of about 80000 cps to about one million cps as measured after storage of the composition at 25° C. for three months.

In various embodiments, said stabilizing agent is further effective to (iv) maintain the microbial count of the composition at a level that meets the criteria of USP 61, as measured by Microbial Limits Testing (MLT) after storage of the composition at a storage condition of 25° C. for six months.

In various embodiments, said stabilizing agent is present in an amount effective to maintain the amount of benzoyl peroxide and the amount of retinoid in the composition at a level of at least about 97% of the initial amounts, as measured after storage of the composition at a storage condition of 5° C. for two years.

In various embodiments, said non-ionic surfactant comprises polyoxyl 100 stearate, glycerol monostearate or a combination thereof.

In various embodiments, said second core further comprises at least one phase changing material selected from the group consisting of a natural paraffin, a synthetic paraffin, an aliphatic alcohol, a fatty acid, an ester of an aliphatic alcohol, and an ester of a fatty acid.

In various embodiments, said ester of a fatty acid comprises a beeswax.

In various embodiments, said second core further comprises an antioxidant.

In various embodiments, said antioxidant is selected from the group consisting of butylated hydroxytoluene (BHT), butylated hydroxyanisole, vitamin E, vitamin E acetate, vitamin E palmitate, vitamin C, an ester of vitamin C, and a salt of vitamin C.

In various embodiments, said first inorganic polymer is different from said second inorganic polymer.

In various embodiments, said first inorganic polymer and said second inorganic polymer are the same.

In various embodiments, said first inorganic polymer and said second inorganic polymer are each independently prepared from a sol-gel precursor selected from the group consisting of tetramethoxysilane, tetraethoxysilane, and sodium silicate.

In various embodiments, the initial amount of said benzoyl peroxide is in the range of about 1% to about 10% by weight, based on the total weight of said composition.

In various embodiments, the initial amount of said benzoyl peroxide is about 6% by weight, based on the total weight of said composition.

In various embodiments, the initial amount of said benzoyl peroxide is about 3% by weight, based on the total weight of said composition.

In various embodiments, the initial amount of said ATRA is in the range of about 0.01% to about 1% by weight, based on the total weight of said composition.

In various embodiments, the initial amount of said ATRA is about 0.1% by weight, based on the total weight of said composition.

In various embodiments, the initial amount of said ATRA is about 0.05% by weight, based on the total weight of said composition.

Another embodiment provides a composition in an emulsion form for topical application, comprising:

a plurality of first core-shell microcapsules comprising a first core that comprises benzoyl peroxide and a first shell that comprises a first silica polymer, the benzoyl peroxide being present in the composition in an initial amount of about 6% by weight, based on the total weight of the composition;

a plurality of second core-shell microcapsules comprising a second core that comprises all-trans retinoic acid (ATRA) and a second shell that comprises a second silica polymer, the ATRA being present in the composition in an initial amount of about 0.1% by weight, based on the total weight of the composition; and a stabilizing agent comprising (a) at least one non-ionic surfactant selected from the group consisting of polyoxyl 100 stearate and glycerol monostearate; and (b) at least one antimicrobial selected from the group consisting of methylparaben and imidazolidinyl urea;

wherein the stabilizing agent is present in an amount effective to:

(ia) maintain the amount of benzoyl peroxide at a level of at least about 5.4% by weight based on the total weight of the composition, as measured after storage of the composition at a storage condition selected from the group consisting of 40° C. for two months, 30° C. for three months, 25° C. for six months and 5° C. for two years;

(ib) maintain the amount of ATRA at a level of at least about 0.09% by weight based on the total weight of the composition, as measured after storage of the composition at a storage condition selected from the group consisting of 40° C. for two months, 30° C. for three months, 25° C. for six months and 5° C. for two years;

(ii) maintain the microbial count of the composition at a level that meets the criteria of USP 51, as measured by Antimicrobial Effectiveness Testing (AET) after storage of the composition at a storage condition of 40° C. for one month; and (iii) maintain the bulk viscosity of said composition at about one million cps or less and within a range of about 70% to about 130% of the initial bulk viscosity, as measured after storage of the composition at 25° C. for three months.

In various embodiments, said stabilizing agent is further effective to (iv) maintain the microbial count of the composition at a level that meets the criteria of USP 61, as measured by Microbial Limits Testing (MLT) after storage of the composition at a storage condition of 25° C. for six months.

Another embodiment provides a composition in an emulsion form for topical application, comprising:

a plurality of first core-shell microcapsules comprising a first core that comprises benzoyl peroxide and a first shell that comprises a first silica polymer, the benzoyl peroxide being present in the composition in an initial amount of about 3% by weight, based on the total weight of the composition;

a plurality of second core-shell microcapsules comprising a second core that comprises all-trans retinoic acid (ATRA) and a second shell that comprises a second silica polymer, the ATRA being present in the composition in an initial amount of about 0.05% by weight, based on the total weight of the composition; and a stabilizing agent comprising (a) at least one non-ionic surfactant selected from the group consisting of polyoxyl 100 stearate and glycerol monostearate; and (b) at least one antimicrobial selected from the group consisting of methylparaben and imidazolidinyl urea;

wherein the stabilizing agent is present in an amount effective to:

(ia) maintain the amount of benzoyl peroxide at a level of at least about 2.7% by weight based on the total weight of the composition, as measured after storage of the composition at a storage condition selected from the group consisting of 40° C. for two months, 30° C. for three months, 25° C. for six months and 5° C. for two years;

(ib) maintain the amount of ATRA at a level of at least about 0.045% by weight based on the total weight of the composition, as measured after storage of the composition at a storage condition selected from the group consisting of 40° C. for two months, 30° C. for three months, 25° C. for six months and 5° C. for two years;

(ii) maintain the microbial count of the composition at a level that meets the criteria of USP 51, as measured by Antimicrobial Effectiveness Testing (AET) after storage of the composition at a storage condition of 40° C. for one month; and (iii) maintain the bulk viscosity of said composition at about one million cps or less and within a range of about 70% to about 130% of the initial bulk viscosity, as measured after storage of the composition at 25° C. for three months.

In various embodiments, said stabilizing agent is further effective to (iv) maintain the microbial count of the composition at a level that meets the criteria of USP 61, as measured by Microbial Limits Testing (MLT) after storage of the composition at a storage condition of 25° C. for six months.

Another embodiment provides a packaged product, comprising a sealable container and the composition as described herein contained within the sealable container.

EXAMPLES

Additional embodiments are disclosed in further detail in the following examples, which are not in any way intended to limit the scope of the claims.

Example 1

Preparation of Encapsulated ATRA (3.06% E-ATRA Water Suspension)

a) Oil Phase 8.62 grams of Butylated hydroxyl toluene (BHT) and 45.9 grams of all-trans retinoic acid (ATRA) were mixed in 129.3 grams of Squalane. 86.16 grams of Tetroethoxysilane (TEOS) were added, and the resulted mixture was milled at 5000 rpm in a ball mill for 10 minutes with an upper propeller mixer at a speed of 250 rpm for 7 minutes, followed by 400 rpm for 3 minutes. 140.4 grams of milled tretinoin in oil was aliquoted out and then heated to 60° C. 9.0 grams of Beeswax were added and melted in the oil phase.

b) Water Phase 3.3 grams CTAC (Cetrimonium Chloride) were dissolved in 490.0 g water at 60° C. Unless indicated otherwise, in all examples described herein, the term "water" refers to sterile water for irrigation (USP).

c) Core-Shell Step 124.5 grams of the oil phase prepared in step (a) was added to the water phase and homogenized at 4000 rpm for 1 minute. 17.9 grams of sodium silicate extra pure solution (28%) were added to the emulsion. The pH of the emulsion was adjusted to 4.0 using HCl 5N solution. Water was added to complete the total weight of the mixture to 650 grams. The suspension was then stirred for 17 hours at 25° C. for the TEOS hydrolysis to be completed. The composition of the final encapsulated ATRA water suspension product is shown in Table 1.

TABLE 1

Composition of the encapsulated ATRA 3.06% water suspension

| Ingredient | % of pure ingredient in the suspension |
| --- | --- |
| Beeswax | 1.15 |
| Squalane | 8.62 |
| TEOS | 5.74 |
| ATRA | 3.06 |
| Cetrimonium Chloride | 0.15 |
| Sodium hydroxide | 0.74 |
| Hydrochloric acid | 0.40 |
| Butylated hydroxytoluene | 0.57 |
| Sterile Water for Irrigation | 79.56 |

Example 2

Preparation of Encapsulated BPO (15% E-BPO Water Suspension)

a) Preparation of Benzoyl Peroxide Solution and Acid Cocktail

A benzoyl peroxide (BPO) solution was prepared by mixing 125.67 grams of CTAC CT-429 (Cetrimonium Chloride 30%), 3008 grams of hydrous benzoyl peroxide, and 5200 grams water under high shear. The solution was homogenized for 60 minutes at 33° C. (no more than 45° C.), and then the pH of the solution was adjusted to 7.0 using sodium hydroxide solution (20%).

An acid cocktail was prepared using 493 grams Hydrochloric acid (37%), 98 grams anhydrous Citric Acid, 147 grams Lactic Acid (90%), and 794 grams water.

b) Coating Cycle

The coating cycle was started by adding 38 grams sodium silicate solution extra pure (28%) to the benzoyl peroxide solution prepared in step a) under high shear, followed by adding the acid cocktail prepared in step (a) to adjust the pH to be lower than 6.8, and followed by adding 57 grams PDAC (3%) solution to the mixture. The cycle was repeated 50 times while the mixture was stirred under high shear for 17 hours. After the 50 cycles, the pH of the mixture was adjusted to 5.0 using the acid cocktail, and water was added to complete the total weight of the mixture to 15 kilograms. The composition of the final BPO water suspension product is shown in Table 2.

TABLE 2

Composition of the encapsulated BPO 15% water suspension

| Ingredient | % of ingredient in the suspension |
|---|---|
| Polyquarternium-7 | 0.53 |
| Hydrochloric Acid | 0.87 |
| Citric Acid, Anhydrous | 0.46 |
| Lactic Acid | 0.63 |
| Silicon Dioxide | 3.42 |
| Sodium hydroxide | 0.01 |
| Cetrimonium Chloride | 0.25 |
| Hydrous Benzoyl Peroxide | 15.00 |
| Sterile Water for Irrigation | 78.83 |

Example 3

Preparation of Formulation of Encapsulated ATRA (0.1%) and Encapsulated BPO (6%) in Emulsion (Formulation I)

Oil Phase: 720.0 of grams Cyclomethicone 5-N, 540.0 of grams Cetyl Alcohol, 360.0 grams Polyoxyl 100 Stearate, and 540.0 grams of Glyceryl Monosterate were mixed at 70° C.

Water phase: 18.0 grams of Ethylendiaminetetraacetate Disodium salt were dissolved in 6500 grams of water. 720.0 grams of glycerin (99.5%) were added to the solution. After the solution was heated to 70° C., 72.0 grams of Carbopol 980 NF were added and the resulting mixture was homogenized at 3300 rpm for 10 minutes to ensure that all materials completely melted and dissolved. 76.5 grams if sodium hydroxide (20%) were then added and the mixture was stirred under high shear for 10 minutes at no less than 70° C.

The oil phase was added to the water phase under high shear at 78° C., and the resulting emulsion was homogenized at 3300 rpm for 10 minutes. 72.0 grams of Citric Acid and 7152 grams of encapsulated BPO 15% water suspension made as described in Example 2 were mixed. The resulting mixture was added to the emulsion at 65° C. and mixed at 1400 rpm for 10 minutes. The emulsion was cooled to 35° C. and the pH of the emulsion was adjusted to 3.5 using HCl 5N solution. After 588.2 grams of encapsulated ATRA 3.06% water suspension made as described in Example 1 were added, the emulsion was stirred at 1400 rpm for 10 minutes. HCl 5N was added to adjust the pH to 3.6, and then water was added until the total weight of the emulsion reached 18 kilograms. The composition of the formulation prepared in this example is shown in Table 3.

TABLE 3

Composition of Formulation I

| Ingredient | % of pure ingredient in the composition |
|---|---|
| Polyquarternium-7 | 0.21 |
| Hydrochloric Acid | 0.51 |
| Citric Acid, Anhydrous | 0.58 |
| Lactic Acid | 0.25 |
| Silicon Dioxide | 1.44 |
| Sodium hydroxide | 0.09 |
| Cetrimonium Chloride | 0.11 |
| Hydrous Benzoyl Peroxide | 6.00 |
| Beeswax | 0.04 |
| Squalane | 0.28 |
| Ethanol (Alcohol) | 0.14 |
| ATRA | 0.10 |
| Butylated hydroxytoluene | 0.02 |
| Glycerin | 4.00 |
| Polyoxyl 100 stearate | 2.00 |
| Cetyl alcohol | 3.00 |
| Cyclomethicone | 4.00 |
| Glyceryl monostearate | 3.00 |
| Edetate Disodium | 0.10 |
| Carbopol 980 | 0.40 |
| Sterile Water for Irrigation | 73.72 |

Example 4

Preparation of Formulation of Encapsulated ATRA (0.1%) and Encapsulated BPO (6%) in Gel (Formulation II)

20.0 grams of PVP (Plasdone K-29/30) and 80 grams of water were mixed to prepare 100 grams of 20% poly vinylpyrrolidone (PVP) solution. 850.0 grams of Glycerin (99.5%) and 7900 grams of water were mixed and stirred for 10 minutes at 2800 rpm. 212.5 grams of Natrosol (250HHX) and 42.5 grams of Klucel (HF Pharm) were added, and the resulted gel was homogenized at 8400 rpm for at least 70 minutes until it was free of lumps. After 17.0 grams of PVP (20%) and 6755 grams of encapsulated BPO 15% water suspension prepared as described in Example 2 were mixed and stirred for 10 minutes, the mixture was added to the gel under high shear. The pH of the gel was then adjusted to 3.5 using HCl 5N. After 6.9 grams of PVP (20%) and 555.55 grams of encapsulated ATRA 3.06% water suspension prepared as described in Example 1 were mixed and stirred for 10 minutes, the mixture was added to the gel and the pH of the gel was then adjusted to 3.5 using HCl 5N. Water was added to complete the total weight of the mixture to 17 kilograms, and the mixture was finally mixed until homogeneity. The composition of the formulation prepared in this example is shown in Table 4.

TABLE 4

Composition of Formulation II

| Ingredient | % of pure ingredient in the composition |
|---|---|
| Polyquarternium-7 | 0.21 |
| Hydrochloric Acid | 0.59 |

TABLE 4-continued

Composition of Formulation II

| Ingredient | % of pure ingredient in the composition |
|---|---|
| Citric Acid, Anhydrous | 0.18 |
| Lactic Acid | 0.25 |
| Silicon Dioxide | 1.44 |
| Cetrimonium Chloride | 0.11 |
| Hydrous Benzoyl Peroxide | 6.00 |
| Beeswax | 0.04 |
| Squalane | 0.28 |
| Ethanol (Alcohol) | 0.14 |
| ATRA | 0.10 |
| Butylated hydroxytoluene | 0.02 |
| Glycerin | 5.00 |
| Hydroxypropyl cellulose | 0.25 |
| Hydroxyethyl cellulose | 1.25 |
| Povidone K-30 (PVP) | 0.03 |
| Sterile Water for Irrigation | 84.32 |

Example 5

Preparation of Encapsulated ATRA (0.635% E-ATRA Water Suspension)

a) Oil Phase 8.62 grams of Butylated hydroxyl toluene (BHT) and 29.7 grams of all-trans retinoic acid (ATRA) were mixed in 145.51 grams of Squalane. 86.17 grams of Tetroethoxysilane (TEOS) were added, and the resulted mixture was milled in a ball mill at 5000 rpm for 10 minutes at 25° C. with an upper propeller mixer at a speed of 250 rpm for 10 minutes. 196.56 grams of milled tretinoin in oil was aliquoted out and then heated to 60° C. 12.6 grams Beeswax were added and melted in the oil phase.

b) Water Phase 5.28 grams of CTAC (Cetrimonium Chloride) were dissolved in 792.0 g of water at 60° C.

c) Core-Shell Step

[199.2 grams of the oil phase prepared in step (a) was added to the water phase and homogenized at 4000 rpm for 1 minute. 28.64 grams of Sodium Silicate extra pure solution (28%) were added to the emulsion. The pH of the emulsion was adjusted to 4.1 using HCl 5N solution. The emulsion was stirred for 17 hours at 25° C., and the pH of the emulsion was at 4.2.

d) Coating Step 960.0 grams of encapsulated ATRA made in step (c) were added to 945.0 grams of water under high shear. 7.68 grams of Sodium Silicate extra pure solution (28%) were added, the pH of the mixture was then adjusted to 2.3 using HCl 5N solution. The coating cycle was repeated for 10 times. After a total of 76.8 grams of Sodium Silicate (25%) was added, 947.2 grams of PDAC-7 (3%) was added and the mixture was homogenized for 10 minutes. The pH of the mixture was adjusted to 4.3 using Sodium Hydroxide 10% solution, and water was added to complete the total weight of the mixture to 2992 grams. The composition of the final ATRA water suspension product is shown in Table 5.

TABLE 5

Composition of the encapsulated ATRA 0.635% water suspension

| Ingredient | % of pure ingredient in the suspension |
|---|---|
| Beeswax | 0.36 |
| Squalane | 3.11 |
| TEOS | 1.84 |
| ATRA | 0.64 |
| Cetrimonium Chloride | 0.05 |
| Silicon Dioxide | 0.93 |
| Hydrochloric acid | 0.29 |
| Polyquantrium-7 | 0.90 |
| Butylated hydroxytoluene | 0.18 |
| Sterile Water for Irrigation | 91.88 |

Example 6

Preparation of Formulations of Encapsulated ATRA (0.1%) and Encapsulated BPO (6%) in Gel (Formulation III)

850.0 grams of Glycerin (99.5%) and 4600 grams of water were mixed and stirred for 10 minutes at 2800 rpm. After 212.5 grams of Natrosol (250HHX) and 42.5 grams of Klucel (HF Pharm) were added sequentially, the resulted gel was homogenized at 8400 rpm for at least 70 minutes until it was free of lumps. 750.0 grams Polyquarternium-7 (10%) were added to 1750.0 grams water to prepare 3% PDAC solution. After 1133.9 grams of 3% PDAC solution and 6666.7 grams of encapsulated BPO 15% water suspension were mixed, the mixture was added to the gel under high shear. The pH of the gel was then adjusted to 3.5 using HCl 5N solution. After 2672.9 grams of encapsulated ATRA 0.635% water suspension prepared according to the procedure described in Example 5 were added, the gel was stirred at 1400 rpm for 15 minutes, and the pH of the gel was then adjusted to 3.6 using HCl 5N solution. After water was added to complete the total weight to 17 kilograms, the mixture was finally mixed until homogeneity. The composition of the formulation prepared in this example is shown in Table 6.

TABLE 6

Composition of Formulation III

| Ingredient | % of pure ingredient in the composition |
|---|---|
| Polyquarternium-7 | 0.54 |
| Hydrochloric Acid | 0.55 |
| Citric Acid, Anhydrous | 0.18 |
| Lactic Acid | 0.25 |
| Silicon Dioxide | 1.59 |
| Cetrimonium Chloride | 0.11 |
| Hydrous Benzoyl Peroxide | 6.00 |
| Beeswax | 0.06 |
| Squalane | 0.49 |
| Ethanol (Alcohol) | 0.22 |
| ATRA | 0.10 |
| Butylated hydroxytoluene | 0.03 |
| Glycerin | 5.00 |
| Hydroxypropyl cellulose | 0.25 |
| Hydroxyethyl cellulose | 1.25 |
| Sterile Water for Irrigation | 83.54 |

Example 7

Preparation of Formulations of Encapsulated ATRA (0.1%) and Encapsulated BPO (6%) in Gel (Formulations IV-VII)

Four additional formulations of encapsulated ATRA and encapsulated BPO were prepared following the procedures as described in the Example section of the International Patent Application PCT/IL2010/001092. The compositions of each of the four formulations prepared in this example are shown in Tables 7-10.

TABLE 7

Composition of Formulation IV

| Ingredient | % of pure ingredient in the composition |
|---|---|
| Polyquarternium-7 | 0.22 |
| Hydrochloric Acid | 0.40 |
| Citric Acid, Anhydrous | 0.18 |
| Lactic Acid | 0.25 |
| Silicon Dioxide | 1.61 |
| Sodium hydroxide | 0.16 |
| Cetrimonium Chloride | 0.11 |
| Hydrous Benzoyl Peroxide | 6.00 |
| Beeswax | 0.06 |
| Squalane | 0.49 |
| Ethanol (Alcohol) | 0.19 |
| ATRA | 0.10 |
| Butylated hydroxytoluene | 0.03 |
| Carbomer 980 | 1.00 |
| Hydroxyethyl cellulose | 0.70 |
| Sterile Water for Irrigation | 88.39 |

TABLE 8

Composition of Formulation V

| Ingredient | % of pure ingredient in the composition |
|---|---|
| Polyquarternium-7 | 0.22 |
| Hydrochloric Acid | 0.40 |
| Citric Acid, Anhydrous | 0.18 |
| Lactic Acid | 0.25 |
| Silicon Dioxide | 1.61 |
| Sodium hydroxide | 0.28 |
| Cetrimonium Chloride | 0.11 |
| Hydrous Benzoyl Peroxide | 6.00 |
| Beeswax | 0.06 |
| Squalane | 0.49 |
| Ethanol (Alcohol) | 0.19 |
| ATRA | 0.10 |
| Butylated hydroxytoluene | 0.03 |
| Carbomer 980 | 1.20 |
| Carbomer 1342 | 0.30 |
| Sterile Water for Irrigation | 88.47 |

TABLE 9

Composition of Formulation VI

| Ingredient | % of pure ingredient in the composition |
|---|---|
| Polyquarternium-7 | 0.22 |
| Hydrochloric Acid | 0.56 |
| Citric Acid, Anhydrous | 0.18 |
| Lactic Acid | 0.25 |
| Silicon Dioxide | 1.61 |
| Sodium hydroxide | 0.01 |
| Cetrimonium Chloride | 0.11 |
| Hydrous Benzoyl Peroxide | 6.00 |
| Beeswax | 0.06 |
| Squalane | 0.49 |
| Ethanol (Alcohol) | 0.19 |
| ATRA | 0.10 |
| Butylated hydroxytoluene | 0.03 |
| Glycerin | 15.00 |
| Hydroxypropyl cellulose | 0.50 |
| Hydroxyethyl cellulose | 1.25 |
| Sterile Water for Irrigation | 73.34 |

TABLE 10

Composition of Formulation VII

| Ingredient | % of pure ingredient in the composition |
|---|---|
| Polyquarternium-7 | 0.56 |
| Hydrochloric Acid | 0.56 |
| Citric Acid, Anhydrous | 0.18 |
| Lactic Acid | 0.25 |
| Silicon Dioxide | 1.61 |
| Sodium hydroxide | 0.01 |
| Cetrimonium Chloride | 0.11 |
| Hydrous Benzoyl Peroxide | 6.00 |
| Beeswax | 0.06 |
| Squalane | 0.49 |
| Ethanol (Alcohol) | 0.19 |
| ATRA | 0.10 |
| Butylated hydroxytoluene | 0.03 |
| Glycerin | 5.00 |
| Hydroxypropyl cellulose | 0.25 |
| Hydroxyethyl cellulose | 1.25 |
| Sterile Water for Irrigation | 83.25 |

Example 8

Stability of Formulations of Encapsulated ATRA and Encapsulated BPO

In this example, formulations that were prepared according to the procedures described in Examples 3, 4, 6 and 7 were stored at 5° C. and 25° C./60% RH, respectively, for three months to evaluate the stability of ATRA and BPO.

ATRA Stability Analysis

Diluent was prepared by dissolving 1 g of BHT in 1000 ml of acetonitrile. ATRA and its degradation products were extracted from each of the formulations with the diluent. The content of ATRA and its unknown degradation products were determined in comparison with an external standard by HPLC method using Agilent 1200 HPLC system or equivalent. The HPLC conditions used are shown in Table 11.

TABLE 11

HPLC Conditions for ATRA Content Analysis

| Column | Zorbax RX-C18 3.5 µm 4.6 * 150 mm | | | |
|---|---|---|---|---|
| Mobile phase | Eluent A - acetonitrile | | | |
| | Eluent B - 1% acetic acid in water | | | |
| | Eluent C - methanol | | | |
| | Time | % A | % B | % C |
| Gradient program | 5 | 50 | 40 | 10 |
| | 25 | 90 | 0 | 10 |

TABLE 11-continued

| HPLC Conditions for ATRA Content Analysis | | | | |
|---|---|---|---|---|
| | 26 | 50 | 40 | 10 |
| | 35 | 50 | 40 | 10 |
| Flow rate | 1.3 ml/min | | | |
| Detection | UV, wavelength 330 nm | | | |
| Injection volume | 10 μL | | | |
| Column temperature | 35° C. | | | |
| Auto-sampler temperature | 4° C. | | | |

The ATRA content in the sample was calculated using the formula:

$$\% \ ATRA = \frac{Asample * V * P}{Rf * Wsample}$$

where:

$A_{sample}$=ATRA peak area arising from the Sample Preparation;
Rf=averaged response factor (area/concentration) (average of five injections of first standard and one injection of second standard);
$W_{sample}$=sample weight in mg;
V=sample solution volume (50 ml);
P=ATRA standard purity in percentage.

The content of individual degradation product (e.g., RRT 0.248, 0.538, 0.560) in the sample as percentage from labeled amount of ATRA (0.1%) was calculated using the formula:

$$\% \ degradation \ product = \frac{Adp * V * P * 100}{Rf * Wsample * 0.1}$$

where:

$A_{dp}$=degradation product peak area arising from the Sample Preparation;
Rf=averaged response factor (area/concentration) (average of five injections of first standard and one injection of second standard);
$W_{sample}$=sample weight in mg;
V=sample solution volume (50 ml);
P=ATRA standard purity in percentage.

The sum of other unknown degradation products in the sample as percentage from labeled amount of ATRA (0.1%) was calculated using the formula:

$$\% \ Sum \ of \ other \ degradation \ product = \frac{\sum Adp * V * P * 100}{Rf * Wsample * 0.1}$$

where:

$\Sigma A_{dp}$=sum of area of other unknown degradation product arising from the Sample Preparation;
Rf=averaged response factor (area/concentration) (average of five injections of first standard and one injection of second standard);
$W_{sample}$=sample weight in mg;
V=sample solution volume (50 ml);
P=ATRA standard purity in percentage.

A summary of the ATRA content of the formulations tested during the three-month storage is shown in Table 12, and a summary of ATRA-related impurities of the formulations tested during the three-month storage is shown in Table 13.

As shown in Tables 12 and 13, the ATRA content is more stable during the three months storage for formulations prepared according to the procedures described in Example 3 and 4 (that is, Formulations I and II) as compared to the formulations prepared according to the procedures described in Examples 6 and 7 (that is, Formulations III-VI). The ATRA contents in Formulations I and II were surprisingly stable during the three months storage at 25° C. The unexpected stability of Formulations I and II indicates that these formulations may be stored at room temperature rather than 5° C. during the product shelf life.

TABLE 12

Stability results based on ATRA content

| Position | T0 ATRA (% w/w) | Freeze/ Thaw ATRA (% w/w) | 5° C. | | | 25° C. | | |
|---|---|---|---|---|---|---|---|---|
| | | | 1 Month ATRA (% w/w) | 2 Months ATRA (% w/w) | 3 Months ATRA (% w/w) | 1 Month ATRA (% w/w) | 2 Months ATRA (% w/w) | 3 Months ATRA (% w/w) |
| Formulation I | | | | | | | | |
| Beginning (3 tubes) | 0.102 | 0.103 | 0.103 | 0.104 | 0.102 | 0.103 | 0.104 | 0.101 |
| Middle (3 tubes) | 0.102 | 0.102 | 0.103 | 0.104 | 0.101 | 0.102 | 0.103 | 0.101 |
| End (3 tubes) | 0.102 | 0.101 | 0.102 | 0.102 | 0.101 | 0.101 | 0.101 | 0.101 |
| Average (9 tubes) | 0.102 | 0.102 | 0.103 | 0.103 | 0.102 | 0.102 | 0.103 | 0.101 |
| % RSD (9 tubes) | 0.5 | 1.0 | 0.7 | 1.0 | 1.0 | 1.0 | 1.0 | 0.5 |
| % Initial Content | 100.0 | 99.9 | 100.7 | 101.3 | 99.7 | 100.2 | 100.6 | 99.0 |
| Formulation II | | | | | | | | |
| Beginning (3 tubes) | 0.101 | 0.101 | 0.102 | 0.098 | 0.101 | 0.101 | 0.101 | 0.100 |
| Middle (3 tubes) | 0.099 | 0.102 | 0.099 | 0.098 | 0.101 | 0.100 | 0.100 | 0.099 |
| End (3 tubes) | 0.099 | 0.101 | 0.100 | 0.099 | 0.100 | 0.100 | 0.101 | 0.099 |
| Average (9 tubes) | 0.099 | 0.101 | 0.100 | 0.099 | 0.100 | 0.100 | 0.101 | 0.099 |
| % RSD (9 tubes) | 2.0 | 1.0 | 1.2 | 1.4 | 1.0 | 1.0 | 1.0 | 0.5 |
| % Initial Content | 100.0 | 101.9 | 101.0 | 99.1 | 100.9 | 101.0 | 101.2 | 99.9 |
| Formulation III | | | | | | | | |
| Beginning (3 tubes) | 0.097 | 0.096 | 0.095 | 0.094 | — | 0.091 | 0.088 | — |
| Middle (3 tubes) | 0.097 | 0.095 | 0.095 | 0.095 | — | 0.091 | 0.088 | — |
| End (3 tubes) | 0.097 | 0.095 | 0.095 | 0.094 | — | 0.091 | 0.087 | — |
| Average (9 tubes) | 0.097 | 0.095 | 0.095 | 0.094 | — | 0.091 | 0.087 | — |
| % RSD (9 tubes) | 1.1 | 0.7 | 0.9 | 0.6 | — | 0.9 | 0.8 | — |
| % Initial Content | 100.0 | 98.4 | 98.3 | 97.5 | — | 93.8 | 90.2 | — |

TABLE 12-continued

Stability results based on ATRA content

| | | Freeze/ | 5° C. | | | 25° C. | | |
|---|---|---|---|---|---|---|---|---|
| Position | T0 ATRA (% w/w) | Thaw ATRA (% w/w) | 1 Month ATRA (% w/w) | 2 Months ATRA (% w/w) | 3 Months ATRA (% w/w) | 1 Month ATRA (% w/w) | 2 Months ATRA (% w/w) | 3 Months ATRA (% w/w) |
| Formulation IV | | | | | | | | |
| Average (3 samples) | 0.105 | — | 0.105 | — | 0.105 | 0.098 | 0.093 | 0.088 |
| % RSD (3 samples) | 0.6 | — | 1.1 | — | 0.5 | 0.6 | <0.1 | 0.7 |
| % Initial Content | 100.0 | — | 100 | — | 100 | 93.9 | 88.9 | 83.8 |
| Formulation V | | | | | | | | |
| Average (3 samples) | 0.104 | — | 0.105 | — | 0.103 | 0.096 | 0.091 | 0.086 |
| % RSD (3 samples) | 1.0 | — | <0.1 | — | 0.6 | 0.6 | <0.1 | 0.7 |
| % Initial Content | 100.0 | — | 101.0 | — | 99.4 | 92.6 | 87.5 | 82.3 |
| Formulation VI | | | | | | | | |
| Average (3 samples) | 0.108 | — | 0.101 | — | 0.103 | 0.099 | 0.099 | 0.093 |
| % RSD (3 samples) | 1.9 | — | 0.6 | — | 1.9 | 1.5 | 1.0 | 1.1 |
| % Initial Content | 100.0 | — | 93.8 | — | 95.4 | 92.0 | 91.7 | 86.1 |
| Formulation VII | | | | | | | | |
| Average (3 samples) | 0.109 | — | 0.108 | — | 0.109 | 0.105 | 0.103 | 0.101 |
| % RSD (3 samples) | 1.6 | — | 0.5 | — | 0.9 | 1.1 | 1.1 | 0.6 |
| % Initial Content | 100.0 | — | 99.4 | — | 100.0 | 96.0 | 94.8 | 92.4 |

TABLE 13

Stability results based on ATRA-related impurities:

| | | Freeze/ | 5° C. | | | 25° C. | | |
|---|---|---|---|---|---|---|---|---|
| Position | T0 % Total Impurities | Thaw % Total Impurities | 1 Month % Total Impurities | 2 Months % Total Impurities | 3 Months % Total Impurities | 1 Month % Total Impurities | 2 Months % Total Impurities | 3 Months % Total Impurities |
| Formulation I | | | | | | | | |
| Beginning (3 tubes) | 0.556 | 0.625 | 0.634 | 0.619 | 0.649 | 0.752 | 0.806 | 0.867 |
| Middle (3 tubes) | 0.388 | 0.661 | 0.678 | 0.613 | 0.515 | 0.685 | 0.953 | 0.934 |
| End (3 tubes) | 0.414 | 0.664 | 0.644 | 0.583 | 0.680 | 0.702 | 0.823 | 0.864 |
| Average (9 tubes) | 0.453 | 0.650 | 0.652 | 0.605 | 0.615 | 0.713 | 0.868 | 0.888 |
| % RSD (9 tubes) | 20 | 7 | 6 | 7 | 14 | 7 | 14 | 5 |
| Formulation II | | | | | | | | |
| Beginning (3 tubes) | 0.586 | 0.472 | 0.447 | 0.396 | 0.600 | 0.778 | 0.638 | 0.818 |
| Middle (3 tubes) | 0.329 | 0.402 | 0.489 | 0.369 | 0.423 | 0.637 | 0.762 | 0.814 |
| End (3 tubes) | 0.361 | 0.436 | 0.521 | 0.351 | 0.642 | 0.650 | 0.660 | 0.822 |
| Average (9 tubes) | 0.426 | 0.437 | 0.476 | 0.372 | 0.555 | 0.688 | 0.687 | 0.818 |
| % RSD (9 tubes) | 30 | 16 | 15 | 12 | 22 | 13 | 11 | 9 |
| Formulation III | | | | | | | | |
| Beginning (3 tubes) | 0.736 | 0.832 | 0.778 | 1.004 | — | 1.614 | 1.929 | — |
| Middle (3 tubes) | 0.765 | 0.854 | 0.861 | 0.959 | — | 1.650 | 1.912 | — |
| End (3 tubes) | 0.767 | 0.829 | 0.835 | 0.980 | — | 1.584 | 1.868 | — |
| Average (9 tubes) | 0.756 | 0.838 | 0.825 | 0.981 | — | 1.616 | 1.903 | — |
| % RSD (9 tubes) | 7 | 9 | 8 | 6 | — | 3 | 3 | — |
| Formulation IV | | | | | | | | |
| Average (3 samples) | 1.801 | — | 0.746 | — | 0.780 | 1.835 | 2.623 | 2.765 |
| % RSD (3 samples) | 3 | — | 3 | — | 5 | 3 | 3 | 2 |
| Formulation V | | | | | | | | |
| Average (3 samples) | 1.860 | — | 1.070 | — | 0.850 | 1.421 | 2.157 | 2.122 |
| % RSD (3 samples) | 9 | — | 7 | — | 2 | 2 | 4 | 2 |
| Formulation VI | | | | | | | | |
| Average (3 samples) | 1.266 | — | 0.472 | — | 0.369 | 0.913 | 1.260 | 1.161 |
| % RSD (3 samples) | 14 | — | 7 | — | 8 | 9 | 9 | 4 |

TABLE 13-continued

Stability results based on ATRA-related impurities:

| Position | T0 % Total Impurities | Freeze/ Thaw % Total Impurities | 5° C. 1 Month % Total Impurities | 5° C. 2 Months % Total Impurities | 5° C. 3 Months % Total Impurities | 25° C. 1 Month % Total Impurities | 25° C. 2 Months % Total Impurities | 25° C. 3 Months % Total Impurities |
|---|---|---|---|---|---|---|---|---|
| | | | Formulation VII | | | | | |
| Average (3 samples) | 0.936 | — | 0.607 | — | 0.494 | 1.114 | 1.597 | 1.462 |
| % RSD (3 samples) | 4 | — | 5 | — | 5 | 4 | 5 | 0 |

BPO Stability Analysis

BPO was extracted from each of the formulations into THF and acetonitrile. The BPO content was determined in comparison with an external standard by HPLC method using Agilent 1200 HPLC system or equivalent. The HPLC conditions used are shown in Table 14.

TABLE 14

HPLC conditions for BPO content analysis

| Column | Zorbax Eclipse XDB-C18 4.6 * 150 mm 5 μm | | |
|---|---|---|---|
| Mobile phase | Eluent A - acetonitrile | | |
| | Eluent B - water | | |
| | Time (min) | Eluent A (%) | Eluent B (%) |
| Gradient conditions | Initial | 60 | 40 |
| | 8 | 60 | 40 |
| | 8.5 | 95 | 5 |
| | 11 | 95 | 5 |
| | 11.1 | 60 | 40 |
| | 16 | 60 | 40 |
| Flow rate | 1.1 ml/min | | |
| Detection | UV, wavelength 254 nm | | |
| Injection volume | 5 μL | | |
| Column temperature | 30° C. | | |

The BPO content in the sample was calculated using the formula:

$$\% \ BPO = \frac{A_{sample} * V * D_{sample} * \%P_{std}}{Rf * W_{sample}}$$

where:

$A_{sample}$=BPO peak area arising from the Sample Preparation;

Dsample=Sample dilution factor (4)

$W_{sample}$=sample weight in mg;

Rf=averaged response factor (area/concentration) (average of five injections of first standard and one injection of second standard);

V=sample solution volume (50 ml);

P=purity of the standard (portion of BPO in the Standard) *(%) (* hydrous BPO Standard contains about 75% BPO)

The changes in BPO content during the three-month storage is summarized in Table 15.

TABLE 15

Summary of stability results based on BPO Content:

| | T0 BPO (% w/w) | Freeze/ Thaw BPO (% w/w) | 5° C. 1 Month BPO (% w/w) | 5° C. 2 Months BPO (% w/w) | 5° C. 3 Months BPO (% w/w) | 25° C. 1 Month BPO (% w/w) | 25° C. 2 Months BPO (% w/w) | 25° C. 3 Months BPO (% w/w) |
|---|---|---|---|---|---|---|---|---|
| | | | | Formulation I | | | | |
| Average (2) | 6.01 | 6.09 | 6.07 | 6.09 | 6.10 | 6.08 | 6.04 | 6.05 |
| % Difference | 0.3 | 0.3 | 0.2 | 0.3 | 0.2 | 0.0 | 0.3 | 0.7 |
| % Initial Content | 100.0 | 101.3 | 100.9 | 101.4 | 101.4 | 101.2 | 100.4 | 100.7 |
| | | | | Formulation II | | | | |
| Average (2) | 6.03 | 6.19 | 5.92 | 6.00 | 6.14 | 5.99 | 6.03 | 6.08 |
| % Difference | 1.5 | 1.1 | 0.0 | 1.0 | 0.5 | 0.5 | 0.2 | 0.7 |
| % Initial Content | 100.0 | 102.7 | 98.3 | 99.5 | 101.8 | 99.3 | 100.1 | 100.9 |
| | | | | Formulation III | | | | |
| Average (2) | 5.93 | 6.11 | 5.79 | 5.95 | — | 5.82 | 5.91 | — |
| % Difference | 0.8 | 2.0 | 0.7 | 0.3 | — | 0.2 | 2.0 | — |
| % Initial Content | 100.0 | 103.1 | 97.7 | 100.4 | — | 98.1 | 99.7 | — |
| | | | | Formulation IV | | | | |
| Average (2) | 6.13 | — | 6.29 | — | 6.33 | 6.24 | 6.22 | 6.19 |
| % Difference | 0.2 | — | 0.3 | — | 0.3 | 0.2 | 1.9 | 0.3 |
| % Initial Content | 100.0 | — | 102.7 | — | 103.3 | 101.8 | 101.6 | 101.1 |

TABLE 15-continued

Summary of stability results based on BPO Content:

|  | T0 BPO (% w/w) | Freeze/Thaw BPO (% w/w) | 5° C. | | | 25° C. | | |
|---|---|---|---|---|---|---|---|---|
|  |  |  | 1 Month BPO (% w/w) | 2 Months BPO (% w/w) | 3 Months BPO (% w/w) | 1 Month BPO (% w/w) | 2 Months BPO (% w/w) | 3 Months BPO (% w/w) |
| Formulation V | | | | | | | | |
| Average (2) | 5.88 | — | 5.92 | — | 5.93 | 5.99 | 5.96 | 5.87 |
| % Difference | 0.5 | — | 0.2 | — | 0.3 | <0.1 | 0.2 | 0.9 |
| % Initial Content | 100.0 | — | 100.7 | — | 100.9 | 102 | 101.4 | 99.8 |
| Formulation VI | | | | | | | | |
| Average (2) | 5.76 | — | 6.06 | — | 6.05 | 5.91 | 5.91 | 5.94 |
| % Difference | <0.1 | — | 0.3 | — | 1.7 | 0.2 | 0.5 | 0.5 |
| % Initial Content | 100.0 | — | 105.2 | — | 105.0 | 102.5 | 102.5 | 103.0 |
| Formulation VII | | | | | | | | |
| Average (2) | 5.82 | — | 6.04 | — | 6.02 | 6.07 | 6.02 | 6.06 |
| % Difference | 0.7 | — | 0.5 | — | 0.8 | 0.8 | <0.1 | 0.2 |
| % Initial Content | 100.0 | — | 103.7 | — | 103.4 | 104.2 | 103.4 | 104.0 |

Example 9

Viscosity of Formulations of Encapsulated ATRA and Encapsulated BPO

Formulations prepared according to the procedures described in Examples 3, 4, 6 and 7 were stored at 5° C. and 25° C./60% RH, respectively, for three months to study their changes in viscosity over time.

For the six formulations prepared according to the procedures described in Examples 4, 6 and 7 (Formulation II—VII), viscosity of each formulation was measured using Brookfield LVDV-II+Pro viscometer under the following conditions: spindle speed 1 rpm, total measuring time: 10 minutes, and temperature 30° C.±0.5° C. For Formulations II and III, spindle #63 (LV3) was used. For Formulations IV-VII, spindle #SC4-25 was used.

For the formulation prepared according to the procedures described in Example 3 (Formulation I), viscosity was measured using Brookfield LVDV-II+Pro viscometer equipped with helipath stand under the following conditions: spindle speed 2 rpm, measuring time interval: 30 seconds, total measuring time: 4 minutes, at room temperature (20° C.-25° C.).

The viscosities of the formulations tested during the three months storage are summarized in Table 16.

TABLE 16

Summary of viscosities during three-month storage

| Storage time (month) | Formulation I | | Formulation II | | Formulation III | |
|---|---|---|---|---|---|---|
|  | 5° C. Viscosity (cps) | 25° C. Viscosity (cps) | 5° C. Viscosity (cps) | 25° C. Viscosity (cps) | 5° C. Viscosity (cps) | 25° C. Viscosity (cps) |
| 0 | 105200 | 105200 | 54600 | 54600 | 77400 | 77400 |
| 1 | 148400 | 154200 | 53880 | 48240 | 73920 | 65160 |
| 2 | 179400 | 168600 | 51480 | 36960 | 64080 | 55440 |
| 3 | 163800 | 166600 | 51240 | 44760 | 77400 | 77400 |

| Storage time (month) | Formulation IV | | Formulation V | | Formulation VI | | Formulation VII | |
|---|---|---|---|---|---|---|---|---|
|  | 5° C. Viscosity (cps) | 25° C. Viscosity (cps) | 5° C. Viscosity (cps) | 5° C. Viscosity (cps) | 5° C. Viscosity (cps) | 25° C. Viscosity (cps) | 5° C. Viscosity (cps) | 25° C. Viscosity (cps) |
| 0 | 415200 | 415200 | 271600 | 271600 | 122800 | 122800 | 109900 | 109900 |
| 1 | 467500 | 457900 | 251500 | 167000 | 123800 | 104100 | 90720 | 68160 |
| 2 | — | 446400 | — | 285100 | — | 90240 | — | 51840 |
| 3 | 474700 | 479500 | 367600 | 390700 | 130500 | 72480 | 88800 | 41280 |

Example 10

Microbial Growth in Formulations of Encapsulated ATRA and Encapsulated BPO

Formulations prepared according to the procedures described in Examples 3 and 4 (Formulations I and II) were stored at 25° C./60% RH for three months to study the microbial growth over time. The results of microbial growth are summarized in Table 17. It was surprising to find that no significant yeast or mold growth in Formulation I (that is, the formulation prepared according to the procedures described in Example 3), which further indicates that this formulation may be stored at room temperature rather than 5° C. during the product shelf life.

TABLE 17

Microbial growth at 25° C. in E-ATRA and E-BPO formulations

| Storage time (month) | | Formulation 1 | Formulation 2 |
|---|---|---|---|
| 0 | Total Aerobic Count | <20 CFU/gram | <20 CFU/gram |
|   | Yeasts and Molds | <20 CFU/gram | <20 CFU/gram |
|   | Specified Microorganisms per 1 g (*Staphylococcus aureus* and *Pseudomonas aeruginosa*) | Absence of *S. aureus* and *P. aeruginosa* | Absence of *S. aureus* and *P. aeruginosa* |
| 1 | Total Aerobic Count | — | — |
|   | Yeasts and Molds | — | — |
|   | Specified Microorganisms per 1 g | — | — |
| 2 | Total Aerobic Count | — | — |
|   | Yeasts and Molds | — | — |
|   | Specified Microorganisms per 1 g | — | — |
| 3 | Total Aerobic Count | <20 CFU/gram | <20 CFU/gram |
|   | Yeasts and Molds | <20 CFU/gram | 20 CFU/gram |
|   | Specified Microorganisms per 1 g | Absence of *S. aureus* and *P. aeruginosa* | Absence of *S. aureus* and *P. aeruginosa* |

Example 11

Antimicrobial Effectiveness Testing of Formulation (I)

Antimicrobial Effectiveness Testing (AET) of Formulation (I) was conducted in accordance with USP 51 at a storage condition of 40° C. for one month. The results are summarized in Table 18 and show that Formulation (I) meets criteria of USP 51.

TABLE 18

AET of Formulation (I) at 40° C.

| | 14 day cfu | Log reduction from initial calculated count at 14 day | 28 day cfu | Log reduction from the 14 day's count at 28 days |
|---|---|---|---|---|
| Bacteria | | | | |
| *S. aureus* | <10 | >4.9 | <10 | 0 |
| *E. Coli* | <10 | >4.6 | <10 | 0 |
| *P. aeruginosa* | <10 | >4.9 | <10 | 0 |
| Yeast and Molds | | | | |
| *C. albicans* | <10 | >5.0 | <10 | 0 |
| *A. niger* | <10 | >4.1 | <10 | 0 |

Example 12

Microbial Limits Testing of Formulation (I) and Formulation (II)

Microbial Limits Testing (MLT) of Formulation (I) and Formulation (II) was conducted in accordance with USP 61 at a storage condition of 25° C. for six months. Briefly, a formulation is considered to meet the criteria of USP 61 when testing under these conditions results in a total bacteria count of not more than 200 cfu and a total yeast and mold count of no more than 20 cfu. Both Formulation (I) and Formulation (II) met this criteria; however the total yeast and mold count for Formulation (II) was 20 cfu. This result indicates a potential for other samples or variants of Formulation (I) and Formulation (II) to not meet the criteria of USP 61, as measured by Microbial Limits Testing (MLT) after storage of the composition at a storage condition of 25° C. for six months, and/or a potential to not meet the criteria of USP 51, as measured by Antimicrobial Effectiveness Testing (AET) after storage of the composition at a storage condition of 40° C. for one month.

Example 13

Preparation of Formulation of Encapsulated ATRA (0.1%) and Encapsulated BPO (6%) in Emulsion with Antimicrobial Stabilizing Agent (Formulation VIII)

Formulation (VIII) was made in a manner similar to that described above in Example 3 for Formulation (I) except that antimicrobials (methyl paraben and imidazolidinyl urea) were included, as follows:

Preparation of Encapsulated ATRA (3.06% E-ATRA Water Suspension)

a) Oil Phase 8.62 grams of Butylated hydroxyl toluene (BHT) and 45.9 grams of all-trans retinoic acid (ATRA) were mixed in 129.3 grams of Squalane. 86.16 grams of Tetroethoxysilane (TEOS) were added, and the resulted mixture was milled at 5000 rpm in a ball mill for 10 minutes with an upper propeller mixer at a speed of 250 rpm for 7 minutes, followed by 400 rpm for 3 minutes. 140.4 grams of milled tretinoin in oil was aliquoted out and then heated to 60° C. 9.0 grams of Beeswax were added and melted in the oil phase.

b) Water Phase 3.3 grams CTAC (Cetrimonium Chloride) were dissolved in 490.0 g water at 60° C. Unless indicated otherwise, in all examples described herein, the term "water" refers to sterile water for irrigation (USP).

c) Core-Shell Step 124.5 grams of the oil phase prepared in step (a) was added to the water phase and homogenized at 4000 rpm for 1 minute. 17.9 grams of sodium silicate extra pure solution (28%) were added to the emulsion. The pH of the emulsion was adjusted to 4.0 using HCl 5N solution. Water was added to complete the total weight of the mixture to 650 grams. The suspension was then stirred for 17 hours at 25° C. for the TEOS hydrolysis to be completed. The composition of the final encapsulated ATRA water suspension product is shown in Table 19.

TABLE 19

Composition of the encapsulated ATRA 3.06% water suspension

| Ingredient | % of pure ingredient in the suspension |
|---|---|
| Beeswax | 1.15 |
| Squalane | 8.62 |
| TEOS | 5.74 |
| ATRA | 3.06 |
| Cetrimonium Chloride | 0.15 |
| Sodium hydroxide | 0.74 |

TABLE 19-continued

Composition of the encapsulated ATRA 3.06% water suspension

| Ingredient | % of pure ingredient in the suspension |
|---|---|
| Hydrochloric acid | 0.40 |
| Butylated hydroxytoluene | 0.57 |
| Sterile Water for Irrigation | 79.56 |

Preparation of Encapsulated BPO (15% E-BPO Water Suspension)

(a) Preparation of Benzoyl Peroxide Solution and Acid Cocktail

A benzoyl peroxide (BPO) solution was prepared by mixing 125.67 grams of CTAC CT-429 (Cetrimonium Chloride 30%), 3008 grams of hydrous benzoyl peroxide, and 5200 grams water under high shear. The solution was homogenized for 60 minutes at 33° C. (no more than 45° C.), and then the pH of the solution was adjusted to 7.0 using sodium hydroxide solution (20%).

An acid cocktail was prepared using 493 grams Hydrochloric acid (37%), 98 grams anhydrous Citric Acid, 147 grams Lactic Acid (90%), and 794 grams water.

(b) Coating Cycle

The coating cycle was started by adding 38 grams sodium silicate solution extra pure (28%) to the benzoyl peroxide solution prepared in step (a) under high shear, followed by adding the acid cocktail prepared in step (a) to adjust the pH to be lower than 6.8, and followed by adding 57 grams PDAC (3%) solution to the mixture. The cycle was repeated 50 times while the mixture was stirred under high shear for 17 hours. After the 50 cycles, the pH of the mixture was adjusted to 5.0 using the acid cocktail, and water was added to complete the total weight of the mixture to 15 kilograms. The composition of the final BPO water suspension product is shown in Table 20.

TABLE 20

Composition of the encapsulated BPO 15% water suspension

| Ingredient | % of ingredient in the suspension |
|---|---|
| Polyquarternium-7 | 0.53 |
| Hydrochloric Acid | 0.85 |
| Citric Acid, Anhydrous | 0.50 |
| Lactic Acid | 0.63 |
| Silicon Dioxide | 3.42 |
| Sodium hydroxide | 0.006 |
| Cetrimonium Chloride | 0.25 |
| Hydrous Benzoyl Peroxide | 15.00 |
| Sterile Water for Irrigation | 78.80 |

Preparation of Formulation (VIII): Encapsulated ATRA (0.1%) and Encapsulated BPO (6%) in Emulsion with Antimicrobials Oil Phase: 720.0 grams of Cyclomethicone 5-N, 540.0 grams of Cetyl Alcohol, 360.0 grams of Polyoxyl 100 Stearate, and 540.0 grams of Mono- and Di-glycerides were mixed at 70° C.

Water phase: 18.0 grams of Ethylendiaminetetraacetate Disodium salt were dissolved in 6500 grams of water. 720.0 grams of glycerin (99.5%), 45.0 grams of methyl paraben, and 45.0 grams of imidazolidinyl urea were added to the solution. After the solution was, mixed at 2800 rpm for 10 minutes, 72.0 grams of Carbopol 980 NF were added and the resulting mixture was homogenized at 3300 rpm for 10 minutes to ensure that all materials completely melted and dissolved. The solution was heated to 70° C. with continuous mixing, 76.5 grams of sodium hydroxide (20%) were then added and the mixture was stirred under high shear for 10 minutes at no less than 70° C.

The oil phase was added to the water phase under high shear at 70° C., and the resulting emulsion was homogenized at 3300 rpm for 10 minutes. 72.0 grams of Citric Acid and 7152 grams of encapsulated BPO 15% water suspension made as described in Example 2 were mixed. The resulting mixture was added to the emulsion at 65° C. and mixed at 1400 rpm for 10 minutes. The emulsion was cooled to 35° C. and the pH of the emulsion was adjusted to 3.5 using HCl 5N solution. After 588.2 grams of encapsulated ATRA 3.06% water suspension made as described in Example 1 were added, the emulsion was stirred at 1400 rpm for 10 minutes. HCl 5N was added to adjust the pH to 3.4-3.7, and then water was added until the total weight of the emulsion reached 18 kilograms. The composition of the formulation prepared in this example is shown in Table 21.

TABLE 21

Composition of Formulation VIII

| Ingredient | % of pure ingredient in the composition |
|---|---|
| Polyquarternium-7 | 0.21 |
| Hydrochloric Acid | 0.51 |
| Citric Acid, Anhydrous | 0.60 |
| Lactic Acid | 0.25 |
| Silicon Dioxide | 1.44 |
| Sodium hydroxide | 0.09 |
| Cetrimonium Chloride | 0.11 |
| Hydrous Benzoyl Peroxide | 6.00 |
| Beeswax | 0.04 |
| Squalane | 0.28 |
| Ethanol (Alcohol) | 0.14 |
| ATRA | 0.10 |
| Butylated hydroxytoluene | 0.02 |
| Glycerin | 4.00 |
| Polyoxyl 100 stearate | 2.00 |
| Cetyl alcohol | 3.00 |
| Cyclomethicone | 4.00 |
| Mono- and Di-Glycerides | 3.00 |
| Edetate Disodium | 0.10 |
| Carbopol 980 | 0.40 |
| Methyl Paraben (antimicrobial) | 0.25 |
| Imidazolidinyl urea (antimicrobial) | 0.25 |
| Sterile Water for Irrigation | 73.21 |

Example 14

Stability of Formulation (VIII) Under Various Storage Conditions

Bulk viscosity, ATRA level and BPO level were measured for samples of compositions prepared as described above in Example 13 for Formulation (VIII) after storage under the indicated conditions. The results are shown in Tables 22-24, respectively.

TABLE 22

Bulk Viscosity Stability of Formulation (VIII)

|  | Initial | 1 Month | 2 Months | 3 Months |
|---|---|---|---|---|
| 5° C. Storage | | | | |
| Bulk Viscosity | 335800 | — | — | 428400 |
| 25° C. Storage | | | | |
| Bulk Viscosity | 335800 | 288800 | — | 258800 |
| 30° C. Storage | | | | |
| Bulk Viscosity | 335800 | 336600 | 301000 | 283600 |

TABLE 23

ATRA Stability of Formulation (VIII)

|  | Initial | 1 Month | 2 Months | 3 Months |
|---|---|---|---|---|
| 5° C. Storage | | | | |
| ATRA (% w/w) - Average (3) | 0.098 | — | — | 0.100 |
| ATRA (% Initial Content) - Average (3) | 100.0 | — | — | 102.0 |
| 25° C. Storage | | | | |
| ATRA (% w/w) - Average (3) | 0.098 | 0.099 | — | 0.094 |
| ATRA (% Initial Content) - Average (3) | 100.0 | 101.0 | — | 95.9 |
| 30° C. Storage | | | | |
| ATRA (% w/w) - Average (3) | 0.098 | 0.092 | 0.092 | 0.088 |
| ATRA (% Initial Content) - Average (3) | 100.0 | 93.9 | 93.9 | 89.8 |

TABLE 24

BPO Stability of Formulation (VIII)

|  | Initial | 1 Month | 2 Months | 3 Months |
|---|---|---|---|---|
| 5° C. Storage | | | | |
| BPO (% w/w) - Average (2) | 5.80 | — | — | 6.00 |
| BPO (% Initial Content) - Average (2) | 100.0 | — | — | 103.4 |
| 25° C. Storage | | | | |
| BPO (% w/w) - Average (2) | 5.80 | 5.96 | — | 5.82 |
| BPO (% Initial Content) - Average (2) | 100.0 | 102.8 | — | 100.3 |
| 30° C. Storage | | | | |
| BPO (% w/w) - Average (2) | 5.80 | 5.90 | 6.02 | 5.81 |
| BPO (% Initial Content) - Average (2) | 100.0 | 101.7 | 103.8 | 100.2 |

Examples 15-33

Effect of Antimicrobial Selection on ATRA Level for Variants of Formulation (VIII)

Figure 2:
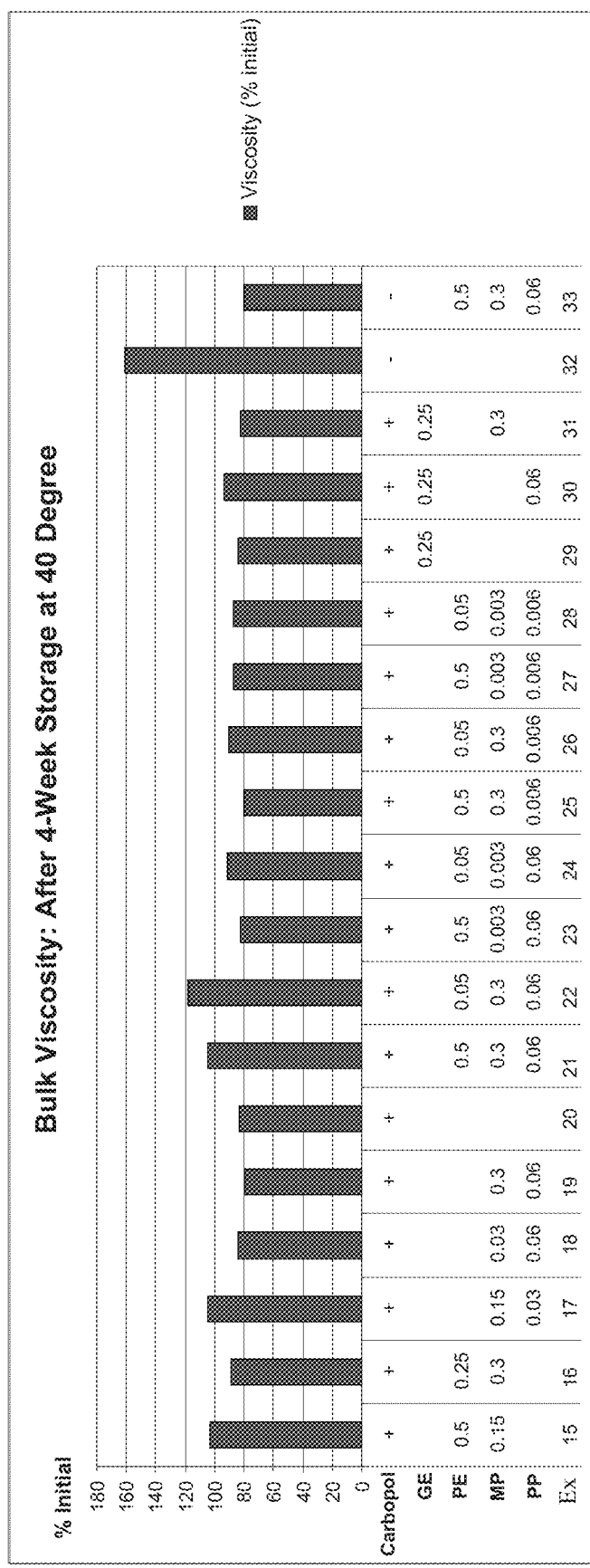
FIG. 2 is a plot illustrating bulk viscosity levels for embodiments of various formulations after 4-week storage at 40° C.
Figure 3:
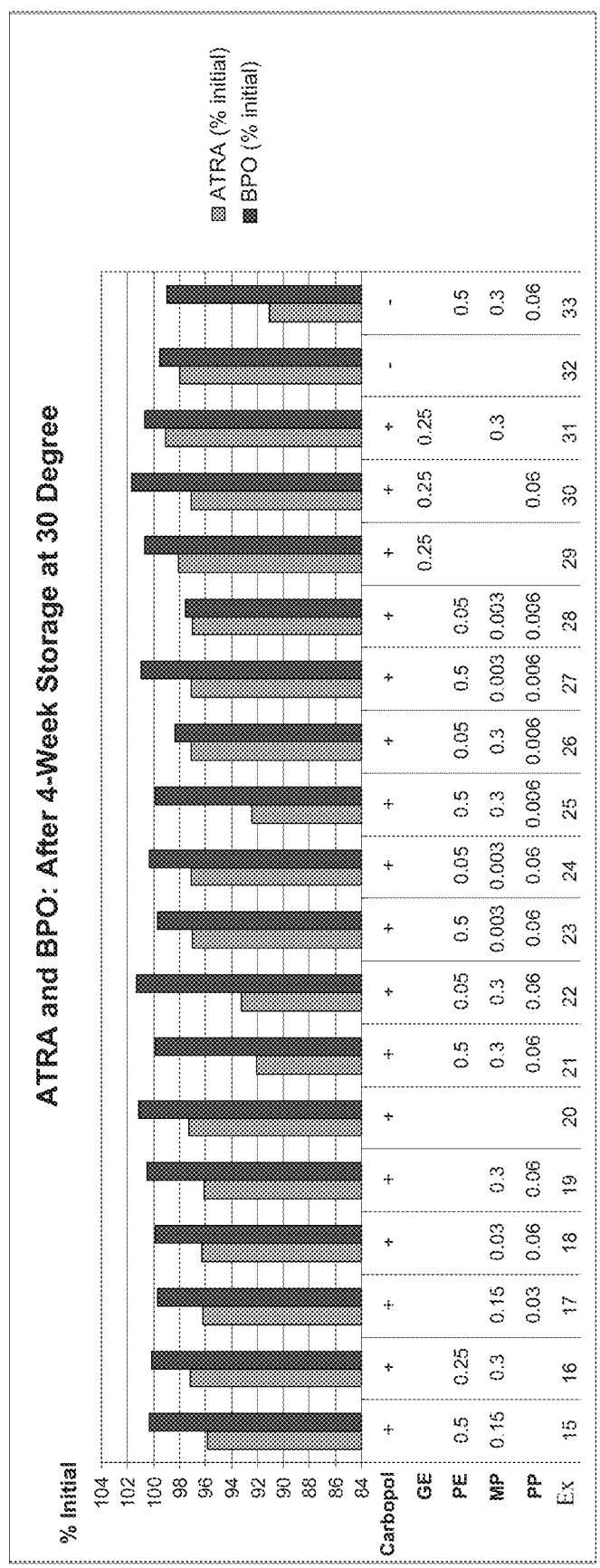
FIG. 3 is a plot illustrating ATRA and BPO levels for embodiments of various formulations after 4-week storage at 30° C.
Figure 4:
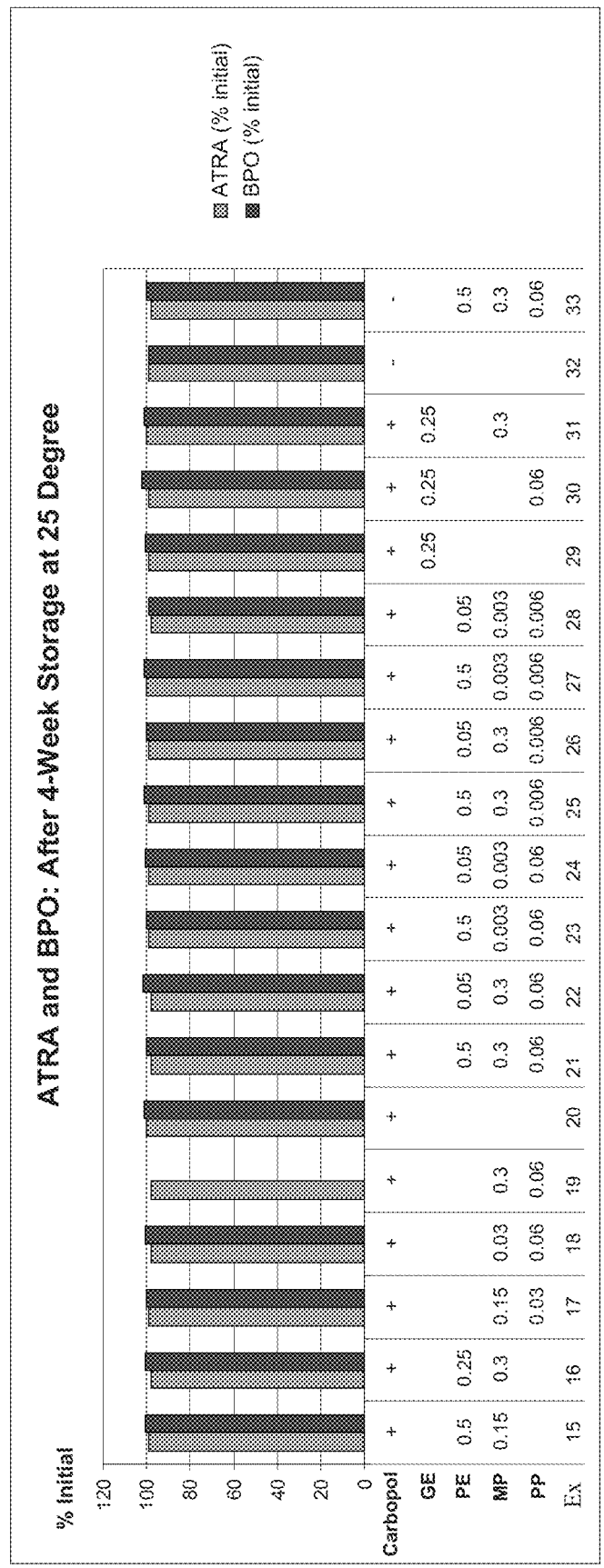
FIG. 4 is a plot illustrating ATRA and BPO levels for embodiments of various formulations after 4-week storage at 25° C.
Figure 5:
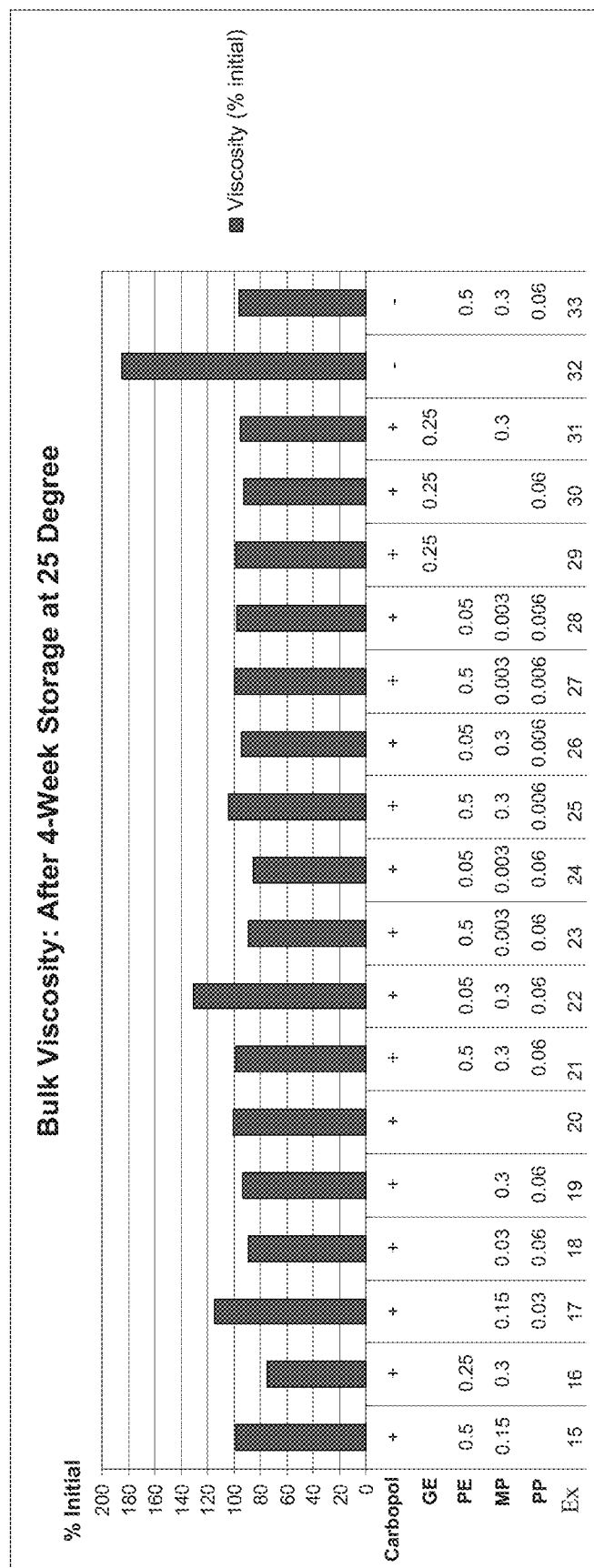
FIG. 5 is a plot illustrating bulk viscosity levels for embodiments of various formulations after 4-week storage at 25° C.

A series of ATRA/BPO formulations (shown in FIGS. 1 through 5) were prepared in a manner similar to that described above in Example 13 for Formulation (VIII) except that the Carbopol content and type and amount of antimicrobial were varied. Measurements of initial bulk viscosity, initial ATRA content and initial BPO content were made. Samples of the ATRA/BPO formulations were then stored for four weeks at 40° C., 30° C. or 25° C. Measurements of bulk viscosity, ATRA content and BPO content were made after storage, and are illustrated in FIGS. 1-5 in terms of the percentage of the initial values. The amount of antimicrobials (wt. % of methylparaben (MP), propylparaben (PP), phenoxyethanol (PE), and/or imidazolidinyl urea (GE)) and the presence (+) or absence (−) of 0.4% Carbopol in each of the formulations are also shown in FIGS. 1-5.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A topical pharmaceutical composition, comprising:
   a plurality of first core-shell microcapsules comprising a first core that comprises benzoyl peroxide and a first shell that comprises a first inorganic polymer, wherein said benzoyl peroxide is in an amount of from about 1% to about 6% by weight based on total weight of the composition, and benzoyl peroxide is the only active agent in said first core; and
   a plurality of second core-shell microcapsules comprising a second core that comprises an oil phase comprising all-trans retinoic acid (ATRA) dispersed in said oil phase and at least one phase changing material, wherein said phase changing material is confined to said second core; and a second shell that comprises a second inorganic polymer, wherein said ATRA is in an amount of from about 0.05% to about 0.5% by weight based on total weight of the composition; wherein ATRA is the only active agent in said second core;
   wherein the concentration of said phase changing material is less than about 10% by weight based on total weight of the composition;
   wherein said phase changing material prevents the leaching of said ATRA from said core into said composition at room temperature;
   wherein said ATRA is stable during the three months storage at 25° C.; and
   wherein said composition is an oil in water emulsion comprising a polyoxylstearate and a glycerylstearate wherein the ratio of said polyoxylstearate to said glycerylstearate is in the range of 2:3 to 3:2;
   wherein said phase changing material is not liquid at room temperature; and
   wherein said second core has a viscosity of from about 5000 cP to about 1,000,000 cP.

2. The composition in accordance with claim 1, further comprising:
   an amount of an anti-microbial agent that is effective to: maintain the microbial count of the composition at a level that meets the criteria of USP 51, as measured by Antimicrobial Effectiveness Testing (AET) after storage of the composition at a storage condition of 40° C. for one month.

3. The composition in accordance with claim 2, wherein:
   said first shell comprises a first silica polymer;
   said second core comprises an oil phase comprising all-trans retinoic acid (ATRA) dispersed in said oil phase and at least one phase changing material; and
   said second shell comprises a second silica polymer.

4. The composition in accordance with claim 2, wherein:
   in said first core-shell microcapsules, said first shell comprises a first silica polymer, and the benzoyl peroxide is present in the composition in an initial amount of about 6% by weight, based on the total weight of the composition;

in said second core-shell microcapsules, said second core comprises an oil phase comprising all-trans retinoic acid (ATRA) dispersed in said oil phase and at least one phase changing material, and said second shell comprises a second silica polymer, the ATRA being present in the composition in an initial amount of about 0.1% by weight, based on the total weight of the composition; and said antimicrobial agent is selected from the group consisting of methylparaben and imidazolidinyl urea.

5. The composition in accordance with claim 2, wherein:

in said first core-shell microcapsules, said first shell comprises a first silica polymer, the benzoyl peroxide being present in the composition in an initial amount of about 3% by weight, based on the total weight of the composition;

in said second core-shell microcapsules, said second core comprises an oil phase comprising all-trans retinoic acid (ATRA) dispersed in said oil phase and at least one phase changing material, and said second shell comprises a second silica polymer, the ATRA being present in the composition in an initial amount of about 0.05% by weight, based on the total weight of the composition.

6. The composition in accordance with claim 1, wherein at least one phase changing material is selected from the group consisting of a natural paraffin, a synthetic paraffin, an aliphatic alcohol, a fatty acid, $C_{10}$-$C_{100}$ alkanes, $C_{10}$-$C_{100}$ alkenes, $C_{10}$-$C_{100}$ alkynes, carnauba wax, beeswax, and a mixture thereof.

7. The composition in accordance with claim 1, wherein said polyoxylstearate is selected from the group consisting of Polyoxyl-8 stearate, Polyoxyl-20 stearate, Polyoxyl-40 stearate, and Polyoxyl-100 stearate.

8. The composition in accordance with claim 1, wherein said glycerylstearate is selected from the group consisting of glyceryl mono-stearate, glyceryl di-stearate and mixtures thereof.

9. The composition in accordance with claim 1, wherein the amount of said polyoxylstearate in said composition is in the range of 0.1% w/w to 30% w/w.

10. The composition in accordance with claim 1, wherein the amount of said glycerylstearate in said composition is in the range of 0.1% w/w to 30% w/w.

11. The composition in accordance with claim 1, wherein said composition further comprises at least one fatty alcohol.

12. The composition in accordance with claim 11, wherein said at least one fatty alcohol is selected from the group consisting of octyl alcohol, 2-ethyl hexanol, nonyl alcohol, decyl alcohol, undecanol, dodecyl alcohol, tridecyl alcohol, tetradecyl alcohol, pentadecyl alcohol, cetyl alcohol, palmitoleyl alcohol, heptadecyl alcohol, cetostearyl alcohol, stearyl alcohol, isostearyl alcohol, elaidyl alcohol, oleyl alcohol, linoleyl alcohol, elaidolinolenyl alcohol, ricinoleyl alcohol, nonadecyl alcohol, arachidyl alcohol, heneicosyl alcohol, behenyl alcohol, erucyl alcohol, lignoceryl alcohol, ceryl alcohol, montanyl alcohol, cluytyl alcohol, myricyl alcohol, melissyl alcohol, geddyl alcohol, cetearyl alcohol and mixtures thereof.

13. The composition in accordance with claim 12, wherein the amount of said at least one fatty alcohol in said composition is in the range of 0.2% w/w to 50% w/w.

14. The composition in accordance with claim 1, wherein said composition further comprises a polyacrylic acid homopolymer or copolymer.

15. The composition in accordance with claim 1, wherein said oil in said oil in water emulsion is selected from the group consisting of paraffin oil, isopropyl myristate, caprylic/capric triglyceride, squalane, squalene, almond oil, castor oil, olive oil, jojoba oil, sunflower oil, soybean oil, grape seed oil, dimethicone, cyclomethicone and mixtures thereof.

16. The composition in accordance with claim 15, wherein said oil is present in the composition in an amount in the range of 0.05% w/w to 50% w/w.

17. The composition in accordance with claim 1, wherein said water in said oil in water emulsion further comprises at least one water soluble humectant.

18. The composition in accordance with claim 17, wherein said at least one water soluble humectant is selected from the group consisting of propylene glycol, glycerin, and polyethylene glycol-X, where X is in the range of 200 to 10,000.

* * * * *